United States Patent [19]

Eida et al.

[11] Patent Number: 5,015,748

[45] Date of Patent: May 14, 1991

[54] NOVEL FERROCENE DERIVATIVES, SURFACTANTS CONTAINING SAME AND A PROCESS FOR PRODUCING ORGANIC THIN FILMS

[75] Inventors: Mitsuru Eida; Yoshio Hiroi; Seiichiro Yokoyama, all of Sodegaura, Japan

[73] Assignee: Idemitsu Kosan Co., Ltd., Tokyo, Japan

[21] Appl. No.: 404,688

[22] Filed: Sep. 8, 1989

[30] Foreign Application Priority Data

Oct. 1, 1988 [JP] Japan .............................. 63-248600
Feb. 28, 1989 [JP] Japan .............................. 1-045370
Mar. 9, 1989 [JP] Japan .............................. 1-054956

[51] Int. Cl.$^5$ ........................................... C07F 17/02
[52] U.S. Cl. .................................... 556/144; 556/143
[58] Field of Search ................ 556/143, 144; 252/351, 252/352, 356; 204/56.1, 59 QM

[56] References Cited

U.S. PATENT DOCUMENTS 3,960,911  6/1976  Suschitzky et al. .................. 556/143
4,749,670  6/1988  Simon et al. .......................... 502/30

FOREIGN PATENT DOCUMENTS 0331745  3/1989  European Pat. Off. .

OTHER PUBLICATIONS

PCT Publication No. WO 89/01939 dated Sep. 3, 1989, Ferrocene Derivatives, Surfactants Containing Same, and Process for Producing Thin Organic Film with English Language Abstract.
Journal of the American Chemical Society, vol. 109, 1987, pp. 5881-5883, American Chemical Society; K. Hoshino et al: "Electrochemical Formation of an Organic Thin Film by Disruption of Micelles", * Whole document *.
Journal of the Chemical Society, Chemical Communications, 1985, pp. 865-866; T. Saji et al.: "Reversible Formation and Disruption of Micelles by Control of the Redox State of the Surfactants Tail Group", * Whole document *.
Chemistry Letters, No. 7, Jul. 1987 pp. 1439-1442, The Chemical Society of Japan; K. Hoshino et al.: "Electrochemical Formation of Thin Film of Viologen by Disruption of Micelles", * Whole document *.
Chemical Abstracts, vol. 104, 1986, p. 533, abstract No. 50983j, Columbus, Ohio, U.S.; & JP-A-60 188 394 (Kawaken Fine Chemicals Co., Ltd.) 25-09-1985, * Abstract *.
Chemical Abstracts, vol. 94, 1981, p. 741, abstract No. 84260m, Columbus, Ohio, U.S.; M. Salisova et al.: "Attempts on Internal Michael Addition of the 1-(Omega-Anisoylalkyl)-1'-Cinnamoylferrocenes", & ACTA FAC. Rerum Nat. Univ. Comenianae, Chim. 1980, 28, 103-26 * Abstract *.
Chemistry Letters, No. 4, Apr. 1988, pp. 693-696, The Chemical Society of Japan, T. Saji: "Electrochemical Formation of a Phthalocyanine Thin Film by Disruption of Micellar Aggregates", * Whole document *.

Primary Examiner—John F. Niebling
Assistant Examiner—Kathryn Gorgos
Attorney, Agent, or Firm—Frishauf, Holtz, Goodman & Woodward

[57] ABSTRACT

Ferrocene compounds represented by the formula:

wherein A indicates (Abstract continued on next page.)

-continued

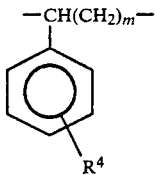

wherein X is —CH$_2$—, —O—,

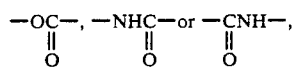

G is a hydrogen atom, a methyl group, or an ethyl group, R$^4$ is a hydrogen atom, a methyl group or an ethyl group, and m is a positive integer satisfying the expression $0 \leq k+m \leq 10$, Z is —O— or

and R$^1$ and R$^2$ are identical or different and each is H, NH$_2$, N(CH$_3$)$_2$, CH$_3$, CH$_3$O, OH or a halogen atom, and R$^3$ is a hydrogen atom or a methyl group, k is a positive integer satisfying the expression $0 \leq k+m \leq 10$, and n is a real number of 2 to 70, a is an integer of 1 to 4, and b is an integer of 1 to 5. Also provided by the invention are surfactants containing said ferrocene compounds. Further provided is a process which comprises making hydrophobic organic substances soluble in an aqueous medium with the use of a surfactant containing the ferrocene compound described above, and electrolyzing the micelle solution thus obtained to form a thin film of the aforementioned hydrophobic organic substance on the electrode. The ferrocene compounds can be used in various applications including surfactants (micelle forming agents), catalysts, auxiliary fuels, flotating agents, lubricating aides, dispersants, liquid crystals and the like.

24 Claims, 11 Drawing Sheets

NOVEL FERROCENE DERIVATIVES, SURFACTANTS CONTAINING SAME AND A PROCESS FOR PRODUCING ORGANIC THIN FILMS

BACKGROUND OF THE INVENTION

1. Field of the Invention

The present invention relates to novel ferrocene derivatives, surfactants containing them and a process for producing organic thin films, and more particularly to novel ferrocene derivatives having a structure with a main carbon chain bonded to ferrocene skeleton in which chain an arylene group such as phenylene is contained or a substituted or unsubstituted phenyl group is bonded as a branch chain; surfactants containing the abovedescribed ferrocene derivatives, and capable of making hydrophobic organic substances including phthalocyanine soluble, and a process for producing a thin film of a hydrophobic organic substance using these surfactants.

2. Description of the Related Arts

In general, coloring materials such as phthalocyanine or its derivatives are insoluble in water, and although they are soluble in organic solvents such as dimethylformamide (DMF), tetrahydrofuran (THF) and the like, their solubility is as small as several milligrams.

Surfactants to dissolve phthalocyanine and the like in water have heretofore been investigated, but a satisfactory one has not been developed. It is reported that phthalocyanine derivatives substituted with a functional group can be dissolved in water to some extent with the use of sulfone-based surfactants. The solubility therein, however, is not always sufficiently high, and, what is worse, unsubstituted phthalocyanines are not dissolved at all.

In connection with water-insoluble polymers, surfactants to make them soluble in water have been investigated similarly to the above, but a satisfactory result has not been obtained.

The present inventors' group have previously developed ferrocene derivatives containing a polyoxyethylene chain as surfactants to make soluble coloring materials such as phthalocyanine, its derivatives, water-insoluble polymers and the like, and at the same time, they have developed a process for forming an organic thin film by applying so-called Micellar Disruption Method by use of said ferrocene derivatives (PCT/JP88/00855) published on Mar. 9, 1989 under WO 89/01939.

The present inventors have made extensive investigations to develop a process for improving the abovementioned surfactants, improving the electrolytic ability in the Micellar Disruption Method while maintaining a high capability of making hydrophobic organic substances soluble, making the oxidation-reduction reaction of ferrocene derivatives proceed smoothly, and further improving the productivity of organic thin films.

As the result, it has been found that the object can be attained by ferrocene derivatives having a novel structure in which an arylene group such as phenylene group is contained in the substituent of the long chain bonded to the ferrocene skeleton, or a substituted or unsubstituted phenyl group is bonded as branch chain to the long chain. The present invention has been completed based on the findings described above.

SUMMARY OF THE INVENTION

An object of the present invention is to provide novel ferrocene derivatives.

Another object of the present invention is to provide surfactants with superior properties, containing the abovementioned novel ferrocene derivatives.

A further object of the present invention is to provide a process for efficiently producing a hydrophobic organic thin film.

The present invention provides novel ferrocene derivatives represented by the general formula:

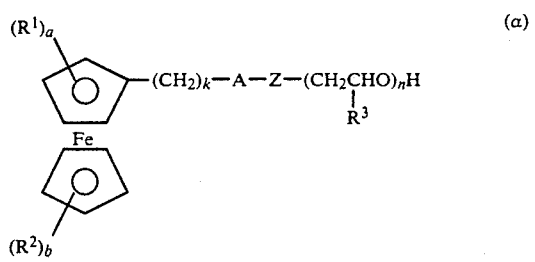

(a)

wherein A indicates

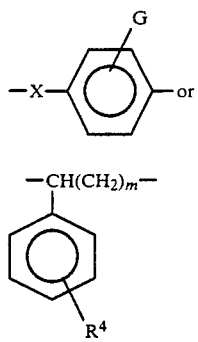

wherein X is —$CH_2$—, —O—,

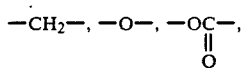

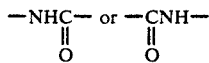

G is a hydrogen atom, a methyl group, or an ethyl group, $R^4$ is a hydrogen atom, a methyl group, or an ethyl group, and m is a positive integer satisfying the expression (1) described below, Z is —O— or

$R^1$ and $R^2$ are each H, $NH_2$, $N(CH_3)_2$, $CH_3$, $CH_3O$, OH or a halogen atom, and $R^3$ is a hydrogen atom or a methyl group, k is a positive integer satisfying the expression:

$$0 \leq k+m \leq 10 \tag{1}$$

and n is a real number of 2 to 70, a is an integer of 1 to 4, and b is an integer of 1 to 5.

The novel ferrocene derivatives represented by the above general formula (α) are divided into two kinds represented by the following formulae (I) and (II).

That is, novel ferrocene derivatives represented by the general formula (I):

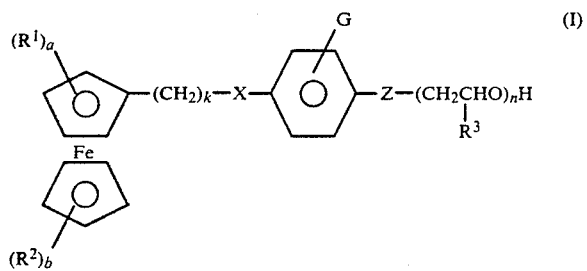

wherein each symbol is as defined above, however, k is a positive integer satisfying $0 \leq k \leq 10$ (when m=0 in the beforementioned expression)
or
novel ferrocene derivatives represented by the general formula (II):

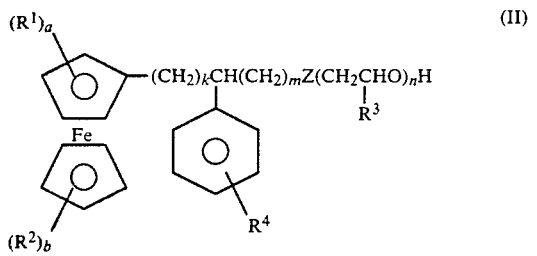

wherein each symbol is defined as above.

Moreover, the present invention provides surfactants containing the novel ferrocene derivatives represented by the general formula (α). Furthermore, the present invention provides a process for solubilizing hydrophobic organic substances, which comprises making hydrophobic organic substances soluble with the use of a surfactant containing the abovementioned novel ferrocene derivatives in an aqueous medium, and a process for producing an organic thin film, which comprises electrolyzing the micelle solution resulting from the said solubilizing process, to form a thin film of the above hydrophobic organic substance on an electrode.

DESCRIPTION OF PREFERRED EMBODIMENTS

Figure 1:
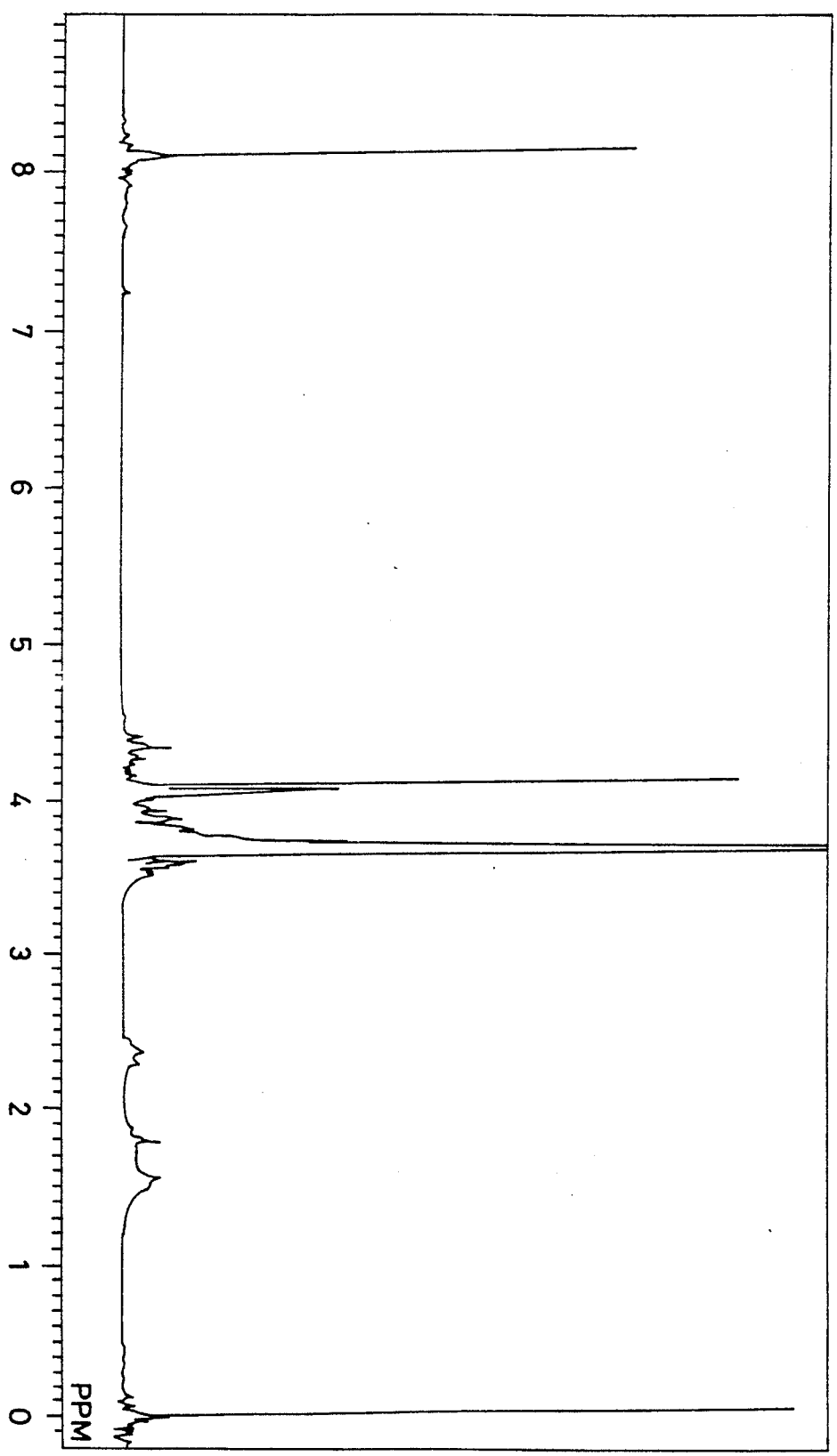
FIG. 1 shows a $^1$H-NMR spectrum of the ferrocene derivative obtained in Example 1.

The ferrocene derivatives of the present invention are represented by the general formula (α), more specifically by the general formula (I) or (II).

First, in the ferrocene derivatives represented by the general formula (I), each symbol in the general formula (I) is as mentioned above. Among them, $R^1$ and $R^2$ are independently a hydrogen atom (H), a methyl group ($CH_3$), a methoxy group ($OCH_3$), an amino group ($NH_2$), a dimethylamino group ($N(CH_3)_2$), a hydroxy group (OH) or a halogen atom (chlorine, bromine, fluorine, etc.), $R^1$ and $R^2$ may be identical or different, and in case where a plural number of $R^1$ and $R^2$ are present at a 5-membered ring of ferrocene, the plural $R^1$ and $R^2$ may be identical or different from each other. The symbol n indicates a recurring number of an oxyethylene group or 1-methyloxyethylene group such as an integer of 2.0 to 70.0 but also a real number including these, and indicates an average value of recurring numbers of the oxyethylene group or 1-methyloxyethylene group.

The novel ferrocene derivatives represented by the above general formula (I) can be produced by various methods. Specifically, these methods can be broadly divided into the following three. These processes for production are shown by the reaction formulae as follows.

Method 1

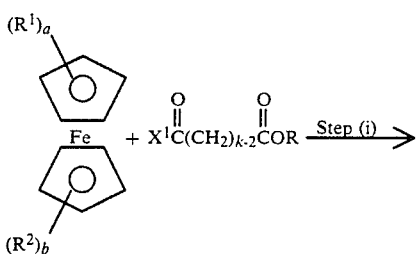

$X^1$ is a halogen atom, and R is a methyl group or an ethyl group.

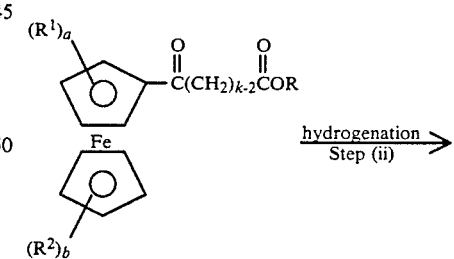

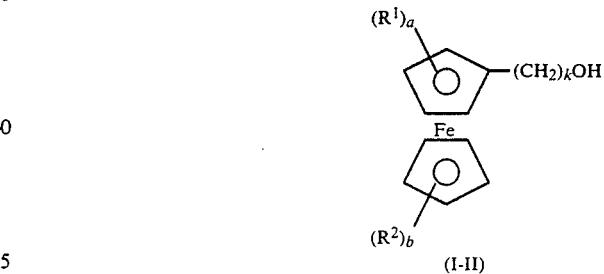

In the reactions up to here, Step (i) is preferably carried out in the temperature range of 0° C. to the reflux temperature in the presence of Lewis acids such as AlCl₃, SbCl₅, FeCl₃, FeCl₂ and SnCl₄, with the use of the solvents such as methylene chloride, carbon disulfide, carbon tetrachloride, and ethylenedichloride. In Step (ii), the reaction is preferred to proceed at room temperature to reflux temperature in the presence of AlCl₃, NaBH₄ or the like, using the solvents such as tetrahydrofuran (THF) and dioxane.

Next, the compound represented by the general formula (I - II) thus obtained is reacted with a compound:

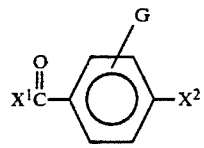
(I-III)

$X^2$ is $$\overset{O}{\underset{\|}{C}}OR$$

or a halogen such as Br
Herein when $X^2$ is $$\overset{O}{\underset{\|}{C}}OR,$$

the following reactions proceed.

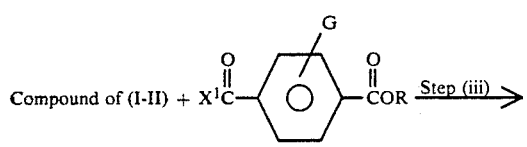
(I-IV)

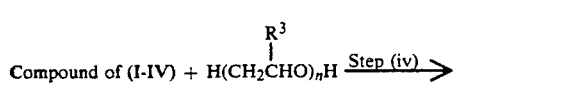
(I-1)

As the result of this reaction, the desired product (I - 1) is obtained. In Step (iii), solvents such as diethylether, THF and dioxane are preferably used, with the use of bases such as triethylamine, pyridine, lutidine and collidine. In Step (iv), it is preferred that dehydration or trans-esterification proceeds while heating by use of potassium t-butoxide, potassium cyanide or sulfuric acid as a catalyst, and further, it is effective to use molecular sieves in order to remove alcohol and other byproducts resulting in the system.

When $X^2$ in the general formula (I - III) is Br, the following reactions proceed.

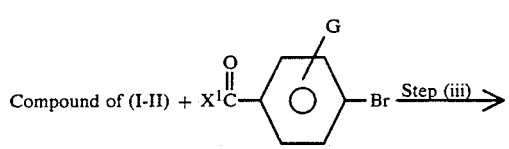

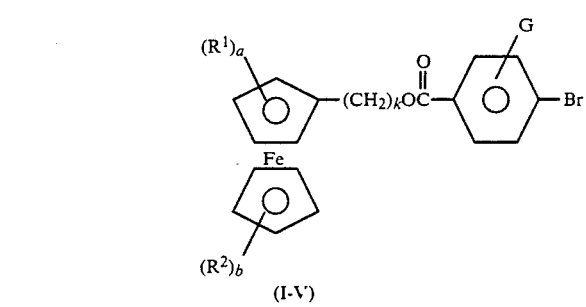
(I-V)

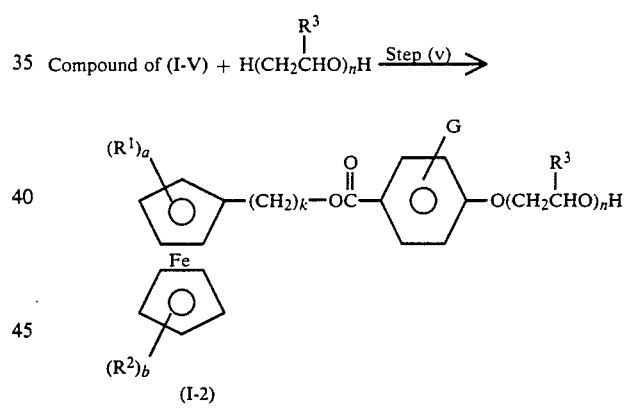
(I-2)

As the result of the above reaction, the desired product (I - 2) is obtained. Therein, in Step (v), it is preferable to use alkali metals (Na, K), bases such as triethylamine, pyridine, lutidine and collidine, and to employ CuI or CuBr as the catalyst.

Method 2

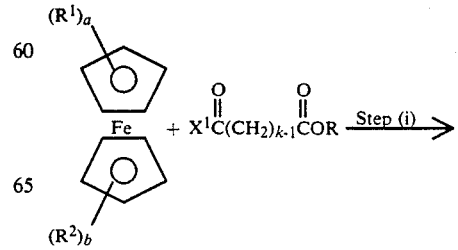

-continued

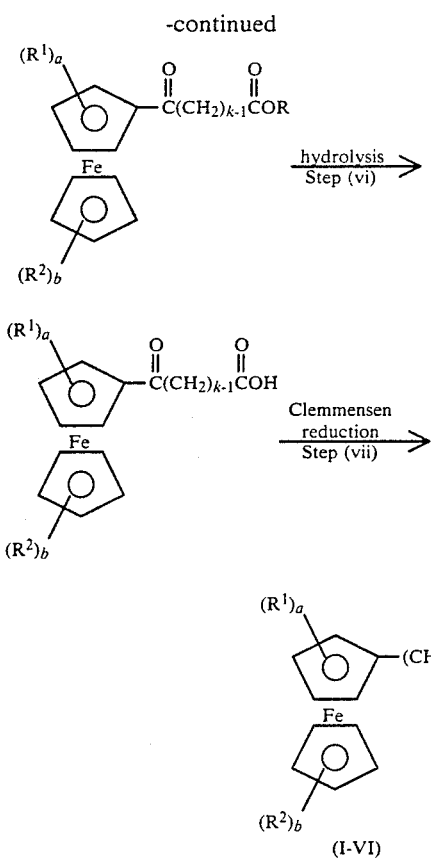

(I-VI)

In the reaction up to here, Step (i) is as mentioned before, and in Step (vi), it is preferred to use alkalis such as KOH and NaOH, and to use solvents such as methanol and ethanol. In Step (vii), further, it is preferred to use common catalysts for a Clemmensen reduction, and to use methanol, ethanol, toluene or acetic acid as the solvents.

The compound of the general formula (I - VI) thus obtained is further subjected to the following reaction.

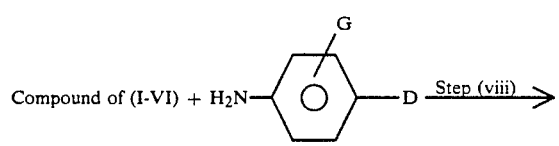

(D is a halogen atom including Br, or $CO_2Q$ (Q is a hydrogen atom, a methyl group or an ethyl group)

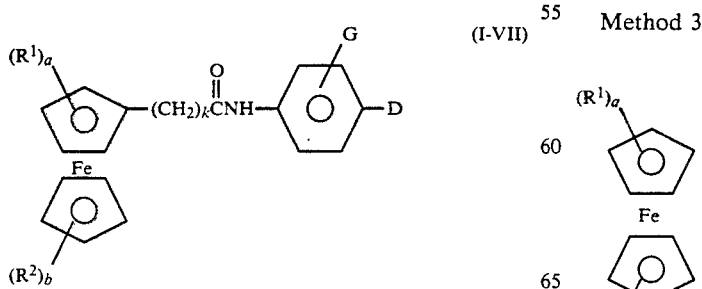

In Step (viii), preferred solvents are methylene chloride, ethylene dichloride or the like, and a preferred example of the condensing agent is 1,3-dicyclohexylcarbodiimide.

Subsequently, the compound represented by the general formula (I - VII) is reacted with a compound:

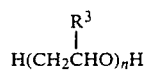

In the general formula (I - VII), when D is a halogen atom including bromine, as the result of a reaction with the use of alkali metals (Na, K) as well as the bases such as triethylamine, pyridine, lutidine and collidine, and using CuI, CuBr or the like as the catalyst, a compound:

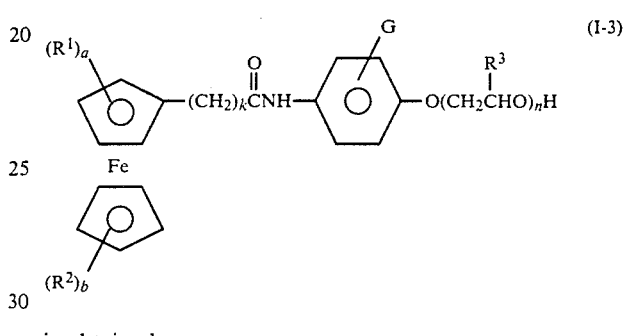

is obtained.

In the general formula (I - VII), in the case where D is $CO_2Q$, when dehydration or trans-esterification is effected using potassium t-butoxide, potassium cyanate or sulfuric acid as the catalyst, and, further, molecular sieves and the like to remove alcohol and other by-products resulting from the reaction system, then a compound:

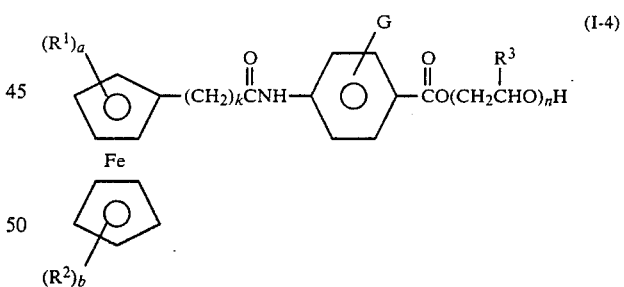

is obtained.

Method 3

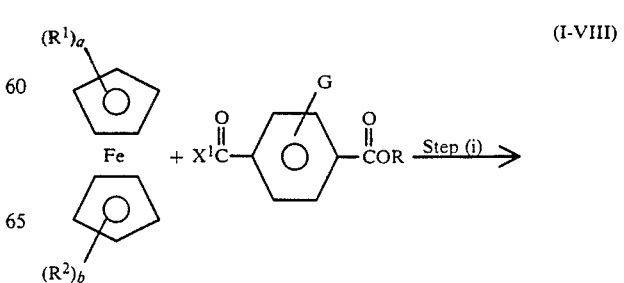

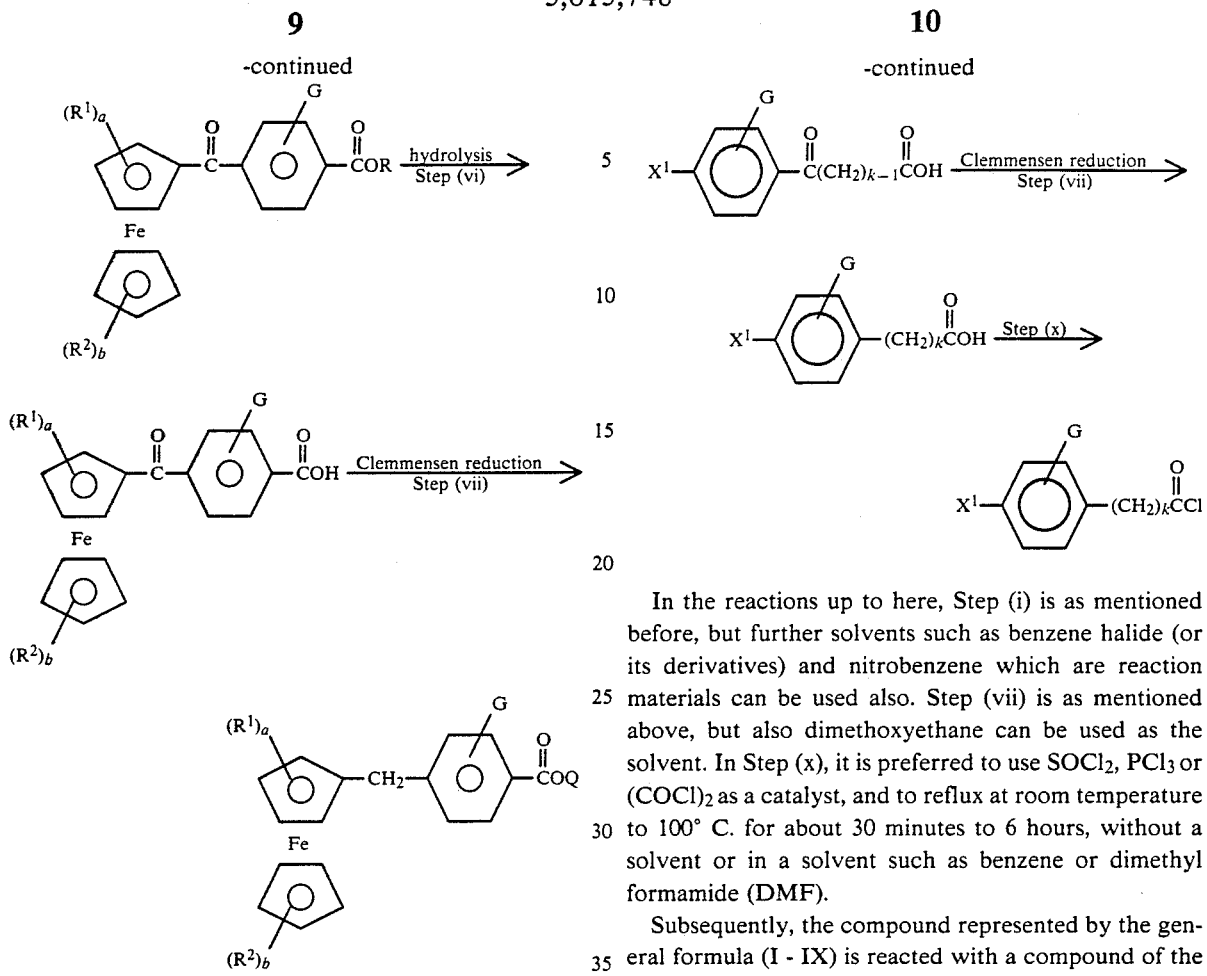

In the above reactions, all of Steps (i), (vi) and (vii) are as mentioned before. Further, by way of the reaction:

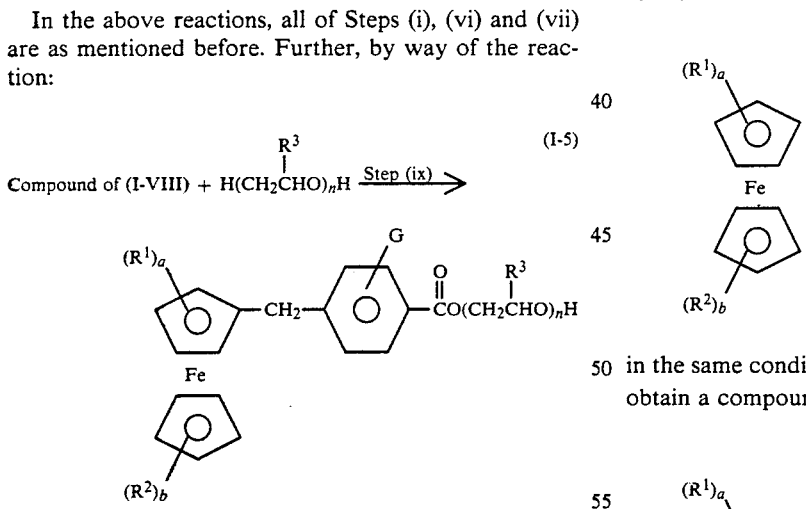

the desired compound represented by the general formula (I - 5) is obtained. In Step (ix), dehydration condensation or trans-esterification proceeds.

Method 4

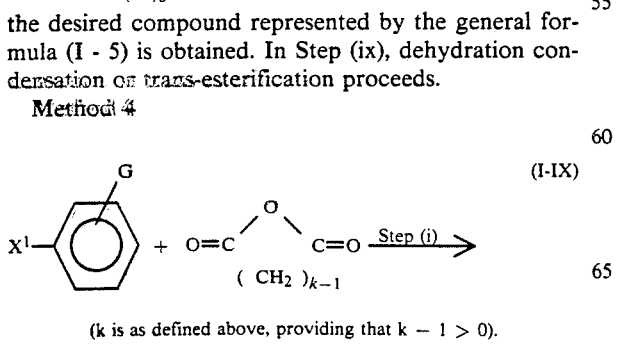

(k is as defined above, providing that k − 1 > 0).

In the reactions up to here, Step (i) is as mentioned before, but further solvents such as benzene halide (or its derivatives) and nitrobenzene which are reaction materials can be used also. Step (vii) is as mentioned above, but also dimethoxyethane can be used as the solvent. In Step (x), it is preferred to use $SOCl_2$, $PCl_3$ or $(COCl)_2$ as a catalyst, and to reflux at room temperature to 100° C. for about 30 minutes to 6 hours, without a solvent or in a solvent such as benzene or dimethyl formamide (DMF).

Subsequently, the compound represented by the general formula (I - IX) is reacted with a compound of the formula:

in the same conditions as in Step (i) described above, to obtain a compound represented by the formula:

Further, a Clemmensen reduction is effected in the same manner as in Step (vii) mentioned before, to produce a compound of the formula:

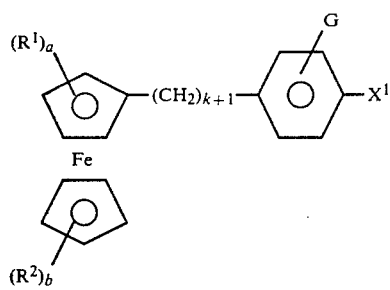

(I-X)

which is reacted with a compound:

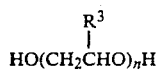

with the use of alkali metals (Na, K) and bases such as triethylamine, pyridine, lutidine and collidine, and at the same time using CuI or CuBr as a catalyst, to obtain the desired compound represented by the formula:

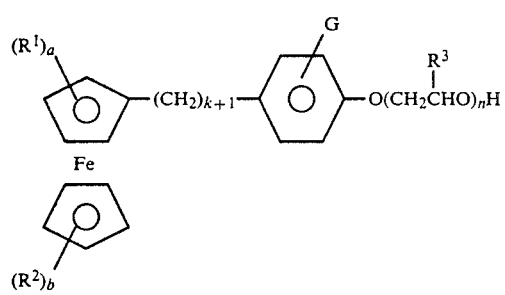

(I-6)

Method 5

With the compound represented by the general formula (I - X), CuCN or NaCN is reacted in the solvents such as DMF, N,N-dimethylformamide and hexamethylphosphoric triamide (HMPA), to obtain a compound of the formula:

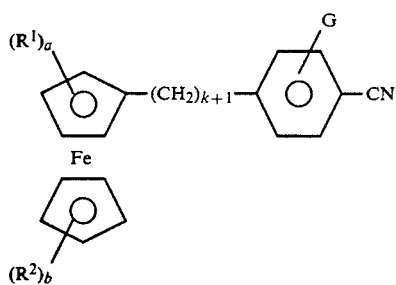

(I-XI)

Therein, above reaction proceeds also without solvents, and use of a catalyst including ferric chloride is also effective. As the reaction, it is sufficient to reflux at the temperature of 100° to 300° C. for a reaction period of about 3 to 20 hours.

Subsequently, the compound of the general formula (I - XI) is reacted with caustic alkali (KOH, NaOH, Ba(OH)$_2$) or concentrated hydrochloric acid for 1 to 20 hours in the reflux conditions of room temperature to 200° C., in the mixed solvent of water and ethanol, the mixed solvent of water and ethylene glycol, or the mixed solvent of water and diethylene glycol, to obtain a compound of the formula:

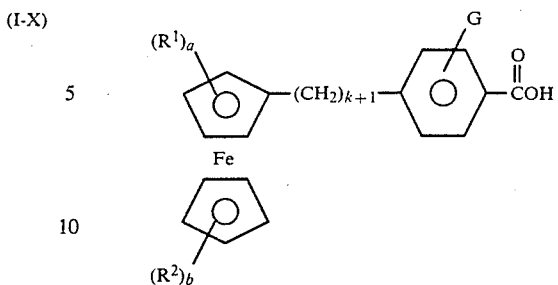

(I-X)

After that, the above compound is reacted with a compound represented by the formula:

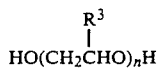

in the presence of a catalyst such as sulfuric acid and p-toluene sulfonic acid, to obtain the desired compound:

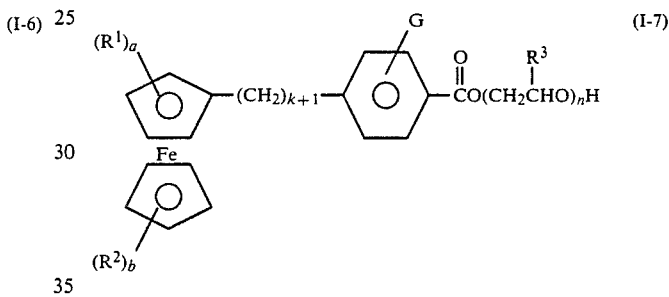

(I-7)

Method 6

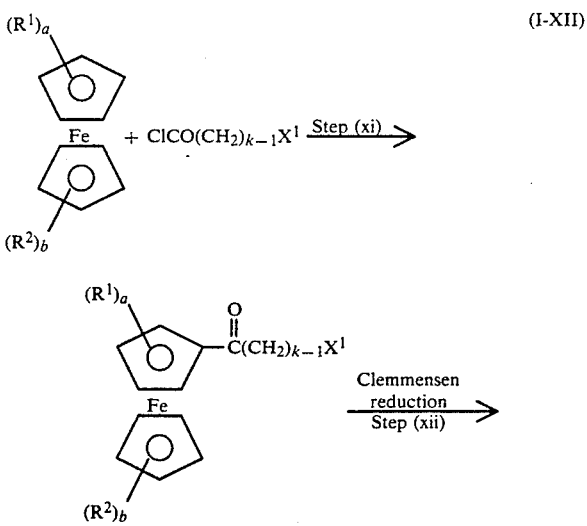

(I-XII)

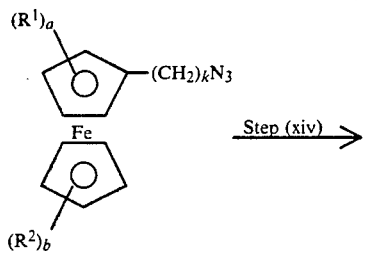

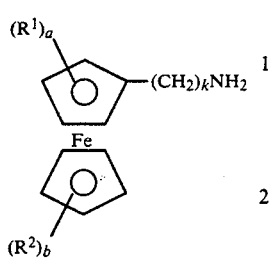

Therein, Step (xi) is almost the same as beforementioned Step (i). Step (xii) is identical to the reaction of the Clemmensen reduction in Method 4 described before. In Step (xiii), the reaction is carried out at 50° to 100° C. for 1 to 30 hours, using a phase-transfer catalyst such as $C_4H_9N^+BF_4^-$ or $C_6H_5CH_2\ N^+(C_2H_5)_3Cl^-$, with sodium azide in aqueous solution. In Step (xiv), hydrogenation is preferably effected in the range of 0° C. to the reflux temperature with the use of a solvent such as diethylether, THF and dioxane, in the presence of LiAlH$_4$.

The compound represented by the general formula (I - XII) thus obtained is further subjected to the following reactions.

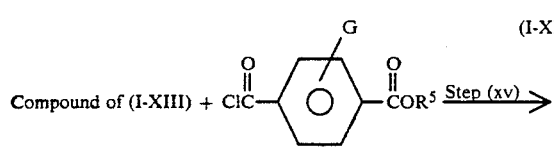

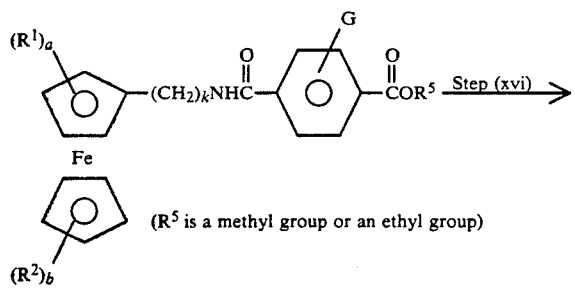

(R$^5$ is a methyl group or an ethyl group)

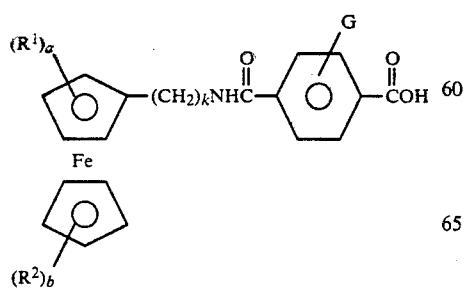

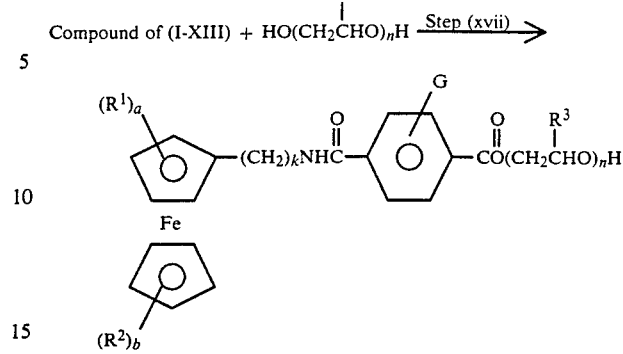

Herein, the reaction in Step (xv) is carried out in an aprotic solvent such as toluene, ether and methylene chloride, in the presence of a tertiary amine catalyst such as triethylamine and pyridine or without a catalyst, at a temperature of −15 to 50° C. for 30 minutes to 8 hours. Step (xvi) is a hydrolysis, which is a reaction at room temperature to 100° C. for 30 minutes to 5 hours, in the presence of caustic alkali (KOH, NaOH, LiOH, etc.) in ethanol, methanol or water as a solvent. Step (xvii) is a reaction at 50° to 200° C. for 3 to 30 hours in the presence of a catalyst such as sulfuric acid and p-toluenesulfonic acid.

According to those methods as above, the novel ferrocene derivatives represented by the general formula (I) (including the general formulae (I - I) to (I - 8)) can be obtained.

Next, the novel ferrocene derivatives represented by the beforementioned general formula (II) will be explained. Each symbol in the general formula (II) is as defined before.

R$^4$ indicates a hydrogen atom, a methyl group (CH$_3$), or an ethyl group (CH$_2$CH$_3$). The position of substitution may be any of o-, m- or p-position. Z is an oxygen atom (—O—) or an oxycarbonyl group

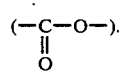

R$^3$ is a hydrogen atom or a methyl group (CH$_3$) as mentioned before.

Accordingly, the general formula:

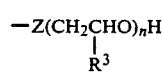

represents:

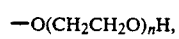

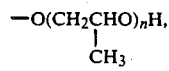

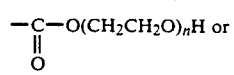

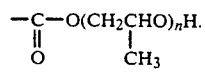

In the length of the main carbon chain having a substituted or unsubstituted phenyl group, bonded to a 5-membered ring of the ferrocene skeleton, that is:

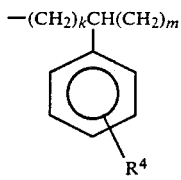

$-(CH_2)_k CH(CH_2)_m$ k and m are each a positive integer satisfying $0 \leq k+m \leq 10$. k is preferably 1 to 5, and m is preferably 1 to 5. Ferrocene derivatives in which $k+m$ is in excess of 10 become poor in electrolytic property.

In the compound of the present invention, the above described main carbon chain is bonded with:

phenyl group 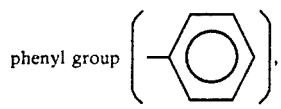, methylphenyl group 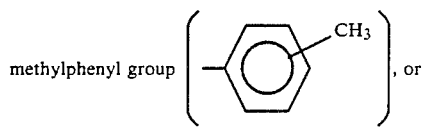, or ethylphenyl group 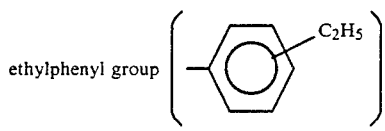

as a branched chain.

Such novel ferrocene derivative represented by the general formula (II) can be produced by various methods. Specifically, when Z is an oxycarbonyl group

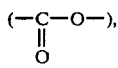

$(-\underset{\underset{O}{\|}}{C}-O-)$, a substituted or unsubstituted ferrocene represented by the general formula:

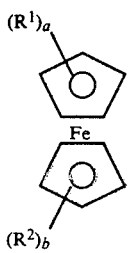

(II-II)

(wherein $R^1$, $R^2$, a and b are as defined above) is reacted in solvents such as methyl chloride, carbon disulfide, carbon tetrachloride and nitrobenzene, with a dicarboxylic acid anhydricde having a substituted or unsubstituted phenyl group, represented by the general formula:

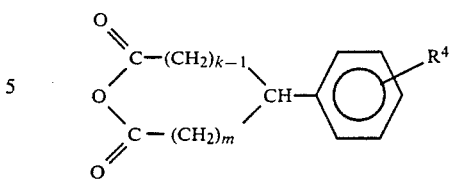

(II-III)

(wherein $R^4$, k and m are as defined above) in the presence of a Friedel-Crafts catalyst (for example, $AlCl_3$, $FeCl_2$, $FeCl_3$, $SbCl_5$ and $SnCl_4$), at $-20°$ C. to the reflux temperature, to obtain a compound represented by the general formula:

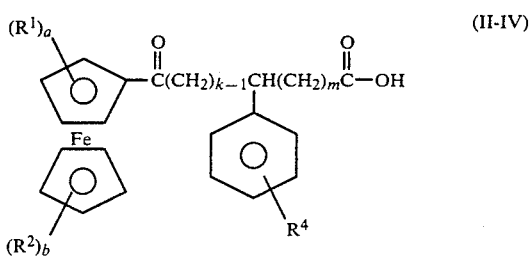

(II-IV)

wherein $R^1$, $R^2$, $R^4$, a, b, k and m are as defined above). Then the compound represented by the above general formula (II - IV) is subjected to a Clemmensen reduction at 20° to 120° C., in the solvents such as alcohol (methanol or ethanol), dimethyl ether, toluene, and acetic acid, using zinc or zinc amalgam and concentrated hydrochloric acid as the reductant, to obtain a compound represented by the general formula:

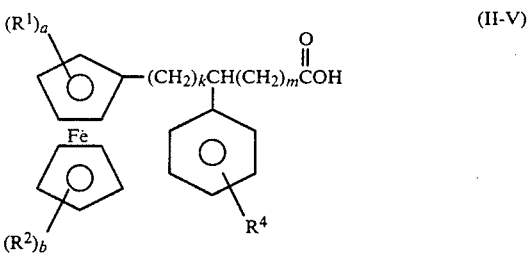

(II-V)

$R^1$, $R^2$, $R^4$, a, b, k and m are as defined above).

After that, the compound of (II - V) is subjected to dehydration-condensation with a polyethylene glycol compound represent by:

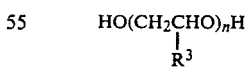

$HO(CH_2CHO)_nH$
$\quad\quad\quad\quad\quad |$
$\quad\quad\quad\quad\quad R^3$ (n and $R^3$ are as defined above), that is $HO(CH_2CHO)_nH$ or

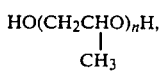

$HO(CH_2CHO)_nH$,
$\quad\quad\quad\quad |$
$\quad\quad\quad\quad CH_3$ in the catalyst such as p-toluene sulfonic acid and sulfuric acid, to produce the desired novel ferrocene derivatives represented by the general formula:

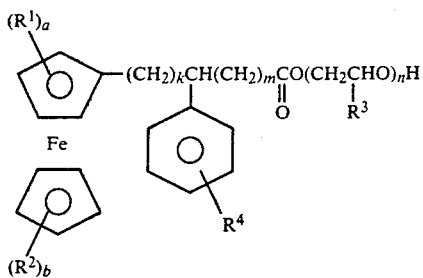

(II')

(wherein $R^1$, $R^2$, $R^3$, $R^4$, a, b, k, m and n are as defined above).

For example, in the case where Z is an oxygen atom (—O—), the compound represented by the general formula (II - II) is reacted with a compound represented by the general formula;

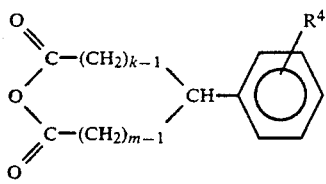

(II-III')

(wherein $R^4$, k and m are as defined above) in the same conditions as in the beforedescribed reaction of the compounds represented by the general formulae (II - II) and (II - III) to obtain the compound represented by the general formula:

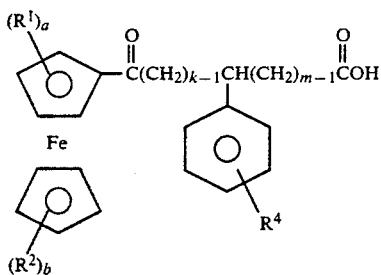

(II-IV')

(wherein $R^1$, $R^2$, $R^4$ a, b, k, and m are as defined above).

subsequently, the compound represented by the general formula (II - IV') is esterificated with methyl alcohol or ethyl alcohol by refluxing for 3 to 10 hours in the catalysts such as p-toluene sulfonic acid or sulfuric acid, to obtain a compound represented by the general formula (II - VI):

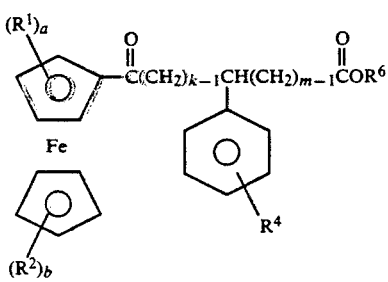

(II-VI)

(wherein $R^1$, $R^2$, $R^4$, a, b, k and m are as defined above, and $R^6$ indicates a methyl group or an ethyl group).

Further, the compound having the general formula (II - VI) is refluxed for 0.5 to 10 hours in an aprotic polar solvent such as tetrahydrofuran, 1,4-dioxane, diethylether, and dimethylether, in the presence of reductants such as sodium borohydride ($NaBH_4$) or lithium aluminum hydride ($LiAlH_4$), to obtain the compound represented by the general formula:

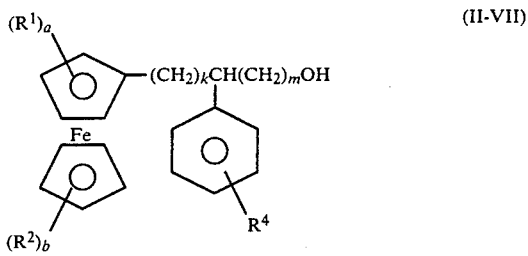

(II-VII)

(wherein $R^1$, $R^2$, $R^4$, a, b, k and m are defined above).

Subsequently, the compound represented by the general formula (II - VII) is halogenated with carbon tetrachloride or carbon tetrabromide by refluxing for 0.5 to 6 hours in a chloroform solvent, in the presence of triphenylphosphine, to obtain a compound represented by the general formula:

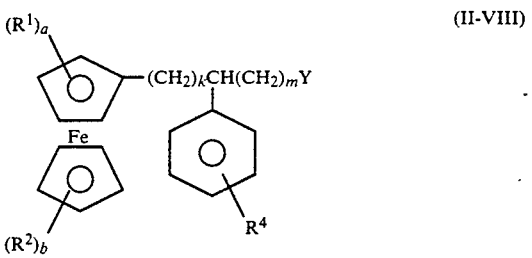

(II-VIII)

(wherein $R^1$, $R^2$, $R^4$, a, b, k and m are as defined above, and Y indicates chlorine or bromine). In that reaction, in the case where carbon tetrachloride is used as a reaction material, said carbon tetrachloride can be used as a solvent.

The compound of the general formula (II - VIII) obtained through the abovementioned reaction is reacted with the polyethylene glycol compound represented by the formula:

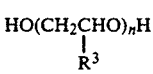

(n and $R^3$ are as defined above.), at 50° to 200° C. for 3 to 30 hours in the presence of alkali metals such as sodium, lithium and potassium, to obtain the novel ferrocene derivatives represented by the general formula:

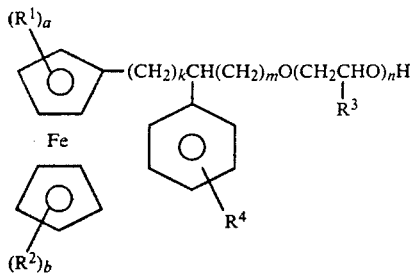

(II″)

(wherein $R^1$, $R^2$, $R^3$, $R^4$, a, b, k, m and n are as defined above).

The novel ferrocene derivatives of the present invention obtained by the abovedescribed processes are useful as surfactants, and can be used particularly as surfactants for making hydrophobic organic substances soluble into aqueous media (micelle forming agents). When used as micelle forming agents, the ferrocene derivatives of the present invention can be used singly or in a mixture of several ferrocene derivatives.

The surfactant of the present invention contains, as main components, the ferrocene derivatives represented by the above general formula ($\alpha$), among them, the general formulae (I), (II) (including the abovementioned general formulae (I - I) to (I - 8), (II'), (II″)), and various additives can be added thereto appropriately, if necessary.

The surfactant of the present invention is capable of making various hydrophobic organic substances soluble into aqueous media. There are various hydrophobic organic substances. Specific examples are, as well as coloring materials for optical memory and organic coloring materials such as phthalocyanine, metal complexes thereof, and derivatives thereof, naphthalocyanine, metal complexes thereof and derivatives thereof, porphyrin and its metal complexes, and derivatives thereof; electrochromic materials such as 1,1- diheptyl-4,4'-bipyridinium dibromide, 1,1'-didodecyl-4,4'-bipyridinium dibromide and the like; light sensitive materials (photochromic materials) and light sensor materials such as 6-nitro-1,3,3-trimethylspiro-(2'H-1'-benzopyran-2,2'-indoline) (commonly called spiropyran) and the like; liquid crystal display coloring materials such as p-azoxyanisole and the like. Further examples are the hydrophobic compounds among the coloring materials each for electronics, recording, light sensitive chromism, photos, energy use, biomedicals, and coloring materials for food and cosmetics, dyes, coloring matters for specific coloring which are listed in "Color Cyclopedia", CMC Co., Ltd., pp 542–717, Mar. 28, 1988. Moreover, other examples are electrically conductive organic materials and gas sensor materials such as the 1:1 complex of 7,7,8,8-tetracyanoquinonedimethane (TCNQ) and tetrathiafulvalene (TTF), light curing paints such as pentaerythritol diacrylate and the like, insulating materials such as stearic acid and the like, diazo-type light-sensitive materials and paints such as 1-phenylazo-2-naphthol and the like. Still further examples are water-insoluble polymers, for examples, general purpose polymers such as polycarbonate, polystyrene, polyethylene, polypropylene, polyamide, polypheylene sulfide (PPS), polypheylene oxide (PPO), polyacrylonitrile (PAN) and the like, polypheylene, polypyrrole, polyaniline, polythiophene, acetyl cellulose, polyvinyl acetate, polyvinyl butyral, and various polymers (polyvinyl pyridine and the like) and copolymers (a copolymer of methyl methacrylate and methacrylic acid).

In the case where the ferrocene derivatives of the present invention are used as surfactants, there are various embodiments. Particularly in the production of the organic thin film of the present invention, they are effectively used as micelle forming agents. In the process of the present invention, a surfactant (micelle forming agent, concentration not lower than the limit micelle concentration) comprising a ferrocene derivative represented by the general formula ($\alpha$), particularly (I) or (II), a supporting salt, and a hydrophobic organic substance are placed in aqueous media and thoroughly dispersed by the use of supersonic waves, a homogenizer, or a stirrer, for example, to form a micelle. This dispersion is conducted usually for 1 hour to 10 days. Thereafter, if necessary, an excessive hydrophobic organic substance is removed, and the micelle solution thus obtained is subjected to electrolytic treatment using the undermentioned electrode while allowing it to stand or stirring it somewhat. During the electrolytic treatment, a hydrophobic organic substance may be supplementally added to the micelle solution, or there may be provided a recycle circuit in which the micelle solution in the vicinity of the anode is withdrawn from the system, a hydrophobic organic substance is added to the withdrawn micelle solution and thoroughly stirred, and then the resulting solution is returned to the vicinity of the cathode. Electrolytic conditions are determined appropriately depending on various circumstances. Usually, the liquid temperature is 0° to 70° C. and preferably 20° to 30° C., the voltage is 0.03 to 100 V and preferably 0.15 to 0.7 V, and the current density is not more than 10 mA/cm$^2$, preferably 50 to 300 $\mu$A/cm$^2$.

On performing this electrolytic treatment, the oxidation-reduction reaction of the ferrocene derivatives proceeds. In connection with the behavior of the Fe ion in the ferrocene derivative, $Fe^{2+}$ is converted into $Fe^{3+}$ on the anode, leading to the breakdown of the micelle, and particles (about 600 to 900 Å) of a hydrophobic organic substance are deposited on the anode. On the other hand, $Fe^{3+}$ oxided on the anode is reduced to $Fe^{2+}$ on the cathode, recovering the original micelle and, therefore, a film forming operation can be carried out repeatedly using the same solution.

Since the novel ferrocene derivatives used in the process of the present invention contain arylene groups such as phenylene group in the main carbon chain, or possess a substituted or unsubstituted phenyl group bonded to the main carbon chain as the branch chain, they have a high ability to make hydrophobic substances soluble, and the beforementioned oxidation-reduction reaction proceeds very efficiently in the said ferrocene derivatives, and accordingly, a thin film can be formed in a short time.

Electrolytic treatment as described above forms a thin film composed of about 600 to 900 Å particles of the desired hydrophobic organic substance on the anode.

The supporting salt (supporting electrolyte) to be used in the process of the present invention is added, if necessary, in order to control the electrical conductance of the aqueous medium. The amount of the supporting salt added is usually about 0 to 300 times, preferably about 10 to 200 times that of the above surfactant (micelle forming agent). Said supporting salt is not always necessary for electrolysis. When the supporting salt is not used, a film of high purity, containing no supporting salt can be obtained. In case a supporting salt is used, the type of the supporting salt is not critical as long as it is capable of controlling the electric conductance of the aqueous medium without inhibiting the formation of the micelle and the deposition of the above hydrophobic organic substance.

More specifically, sulfuric acid salts (salts of lithium, potassium, sodium, ribidium or aluminum) and acetic acid salts (salts of lithium, potassium, sodium, ribidium, beryllium, magnesium, calcium, strontium, barium or aluminum), halides, (salts of lithium, potassium, sodium, rubidium, calcium, magnesium, or aluminum), and water-soluble oxide salts (salts of lithium, potassium, sodium, rubidium, calcium, magnesium or aluminum), which are generally widely used as supporting salts, are suitable.

The electrode to be used in the process of the present invention is sufficient to be a metal more noble than the oxidation potential (against +0.15 V saturated calomel electrode) of ferrocene, or an electrically conductive substance. Specific examples are ITO (mixed oxide of indium oxide and tin oxide), platinum, gold, silver, glassy carbon, electrically conductive metal oxides, electrically conductive organic polymers and the like.

The ferrocene derivatives of the present invention are novel compounds and can be used in various fields, for example, as surfactants (micelle forming agent), catalysts, auxiliary fuels, flotation agents, lubricating aids, dispersants, liquid crystals and the like. The novel ferrocene derivatives, when used as surfactants (micelle forming agents), form micelles in an aqueous solution system and, therefore, can make soluble various hydrophobic organic substances such as coloring materials including phthalocyanine, having a wide variety of applications and water-insoluble polymers.

According to the process of the present invention, in which ferrocene derivatives are added as surfactants (micelle forming agents) and the gathering or scattering of micelles by aqueous solution electrolysis are utilized, an organic thin film extremely small in thickness can be formed. In this process, the film is formed in a very high productivity since the oxidation-reduction efficiency of the said surfactant is excellent.

The organic thin film formed according to the process of the present invention can be effectively utilized in various fields including photoconductor materials, light-sensitive materials and solar batteries.

The present invention will be explained in more detail by referring to Examples and Comparative Examples.

PREPARATION EXAMPLE 1

(1) An acid chloride prepared by reacting 25.0 g of glutaric monomethyl ester and 50.0 ml of thionyl chloride was reacted with 34.0 g of aluminum chloride and 31.8 g of ferrocene at 50° C. for 3 hours in a methylene chloride solvent.

After completion of the reaction, the reaction mixture was treated with water, extracted with ethyl acetate, and then purified with a silcia gel column chromatogrtaphy to obtain 38.8 g of methyl-4-ferrocenoyl butyrate represented by the following formula:

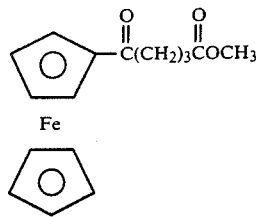

(2) An amount of 38.8 g of methyl-4-ferrocenoyl butyrate prepared in (1) above, 54.7 g of aluminum chloride and 25.9 g of sodium borohydride were heat-refluxed for 2 hours in a tetrahydrofuran solvent.

After completion of the reaction, the reaction mixture was treated with dilute hydrochloric acid, extracted with ethyl acetate and purified with a silica gel column chromatography to obtain 22.0 g of 5-ferrocenylamyl alcohol represented by the following formula:

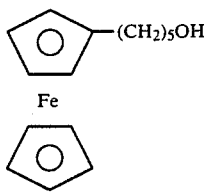

(3) An amount of 2.7 g of 5-ferrocenylamyl alcohol obtained in (2) above, 1.9 g of terephthaloyl monomethoxy monochloride and 1.4 ml of triethylamine were stirred in ether at room temperature for 2 hours, to obtain 3.2 g of p-(5-ferrocenylamyloxycarbonyl)-benzoic acid methyl ester represented by the formula:

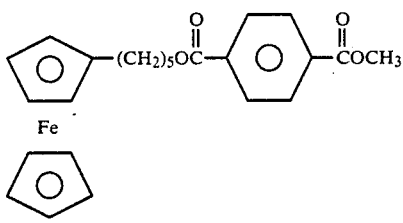

EXAMPLE 1

An amount of 2.7 g of p-(5-ferrocenylamyloxycarbonyl)benzoic acid methyl ester prepared in Preparation Example 1 was reacted with 30.0 g of polyethylene glycol (average molecular weight: 600), 5 g of molecular sieves 5A and 0.01 g of potassium tert-butoxide, at 80° C. for 5 hours.

After completion of the reaction, the reaction mixture was treated with water, and extracted with n-butanol saturated with water. Subsequently the extract was concentrated, and subjected to a silica gel column chromatography by the use of a mixed solvent of ethyl acetate and methanol (ethyl acetate : methanol = 3:1), to obtain 2.83 g of the desired product in a yield of 45%.

The elemental analytical values of the product were: carbon, 58.9%; hydrogen, 7.3%; nitrogen, 0.0%. The results of measurement of proton nuclear magnetic resonance ($^1$H-NMR) spectrum are as shown in FIG. 1.

From the above results, it can be seen that the above resulting compound was a ferrocene derivative having the following structure:

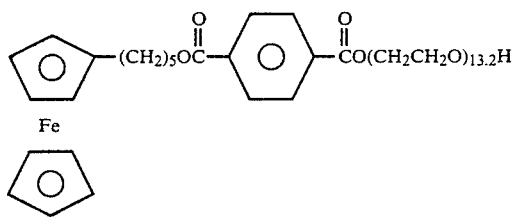

PREPARATION EXAMPLE 2

(1) In the presence of 11.2 g of anhydrous aluminum chloride, 14.1 g of ferrocene and 15.0 g of terephthaloyl monomethoxy monochloride were reacted at room temperature for 2 hours in a methylene chloride solvent.

After completion of the reaction, the reaction mixture was treated with dilute hydrochloric acid and then purified with a silica gel column chromatography to obtain 12.6 g of methyl-p-ferrocenoyl benzoate represented by the formula:

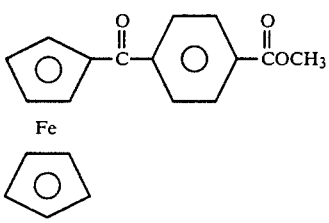

(2), An amount of 6.3 g of methyl-p-ferrocenoyl benzoate prepared in (1) above and 1.8 g of potassium hydroxide were refluxed for 2 hours in an ethanol solvent and then subjected to acid treatment to obtain 6.0 g of p-ferrocenoyl benzoic acid represented by the formula:

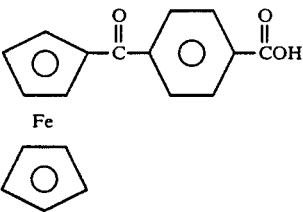

(3) In the presence of zinc amalgam prepared from 6.5 g of zinc and 2.7 g of mercuric chloride, 6.0 g of p-ferrocenoyl benzoic acid prepared in (2) above was reacted at 80° C. for 3 hours in a mixed solvent of concentrated hydrochloric acid and ethanol.

After completion of the reaction, the reaction mixture was extracted with ethyl acetate and purified with a silica gel column chromatography to obtain 3.0 g of p-ferrocenylmethyl benzoic acid ethyl ester represented by the formula:

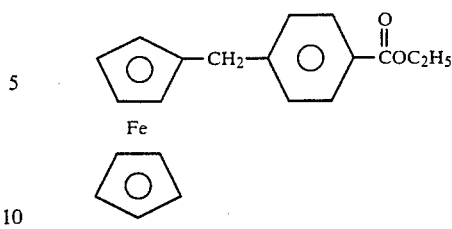

EXAMPLE 2

An amount of 1.0 g of p-ferrocenylmethyl benzoic acid ethyl ester prepared in Preparation Example 2 and 29.0 g of polyethylene glycol (average molecular weight : 1000) were reacted with 0.2 ml of concentrated sulfuric acid, at 110° C. for 10 hours.

After completion of the reaction, the reaction mixture was washed with water, extracted with n-butanol saturated with water, and the concentrated extract was purified with a silica gel column chromatography using a mixed solvent of ethyl acetate and methanol (ethyl acetate : methanol=3:1), to obtain 1.3 g of the desired substance in a yield of 30.2%.

Figure 2:
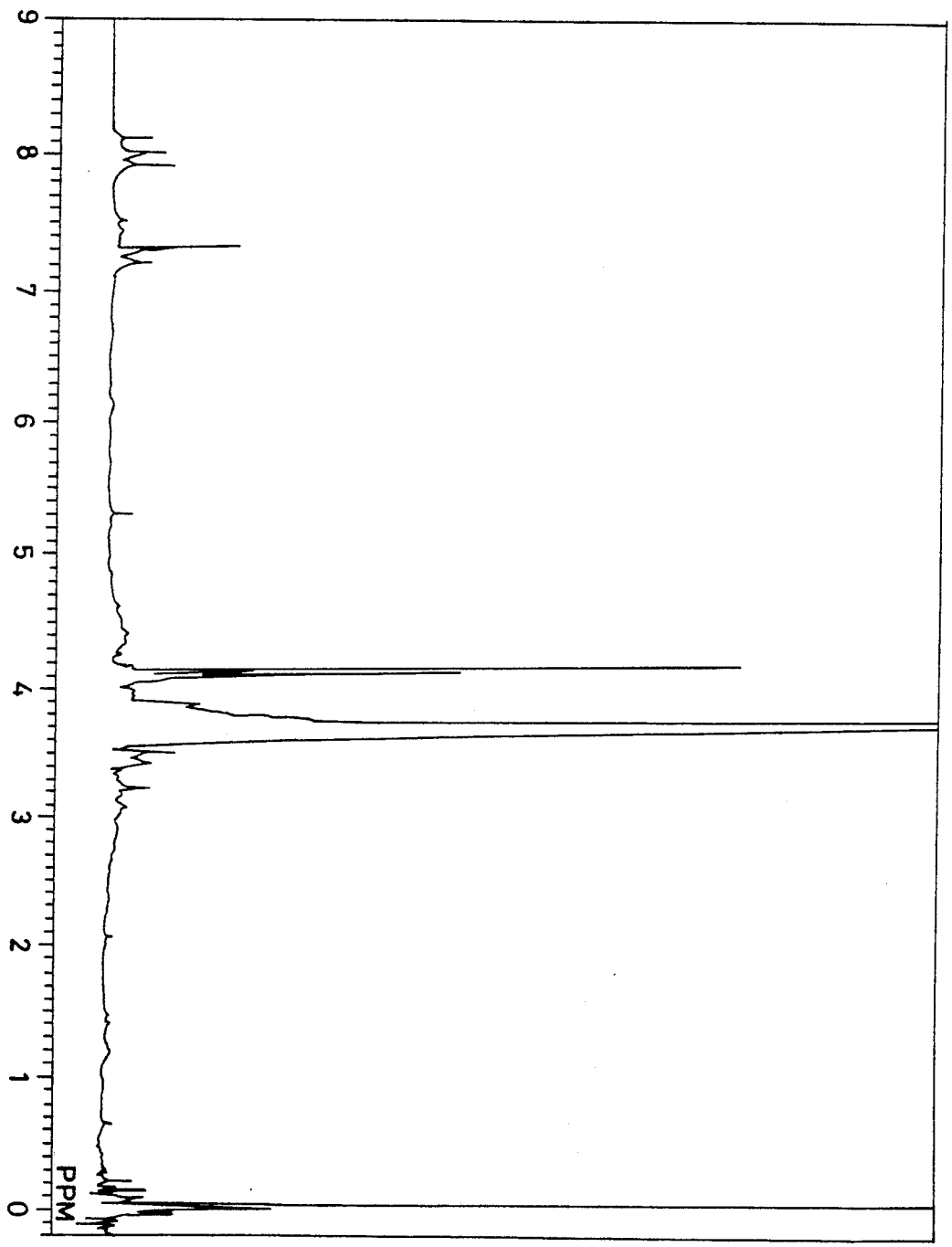
FIG. 2 and FIG. 3 show a $^1$H-NMR spectrum of the ferrocene derivative obtained in Example 2 and Example 3, respectively.

The elemental analytical values were: carbon, 58.2%; hydrogen, 8.3%; nitrogen, 0.00%. The results of measurement of proton nuclear magnetic resonance spectrum were as shown in FIG. 2.

These results show that the product was a ferrocene derivative having the following structure:

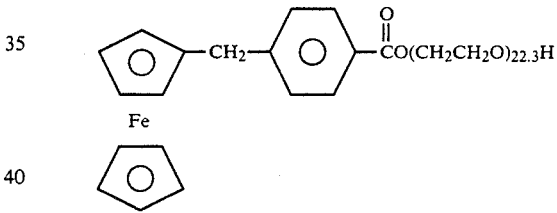

PREPARATION EXAMPLE 3 (1) An amount of 25.8 g of methyl-4-ferrocenoyl butyrate prepared according to the method of Preparation Example 1 (1) was reacted in ethanol with 11.5 g of potassium hydroxide, to obtain 24.0 g of 4-ferrocenoyl butyric acid represented by the following formula:

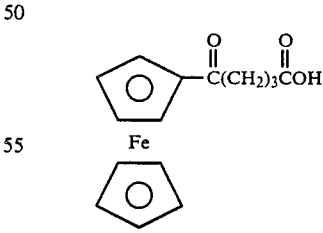

(2) In the presence of zinc amalgam prepared from 52.3 g of zinc and 21.7 g of mercuric chloride, 24.0 g of 4-ferrocenoyl butyric acid prepared in (1) above was reacted at 80° C. for 3 hours in a mixed solvent of concentrated hydrochloric acid and ethanol.

After completion of the reaction, the reaction mixture was extracted with ethyl acetate and purified with a silica gel column chromatography to obtain 16.0 g of 5-ferrocenoyl valeric acid represented by the formula:

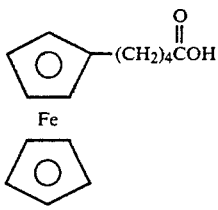

(3) To 16.0 g of 5-ferrocenoyl valeric acid prepared in (1) above, 12.0 g of 1,3-dicyclohexylcarbodiimide was added in a dichloroethane solvent. Further, 7.7 g of p-aminobenzoic acid was added to the resulting mixture, and reacted while heating from 0° C. to the reflux temperature.

After completion of the reaction, the reaction mixture was extracted with ethyl acetate and purified with a silica gel column chromatography, to obtain 10.9 g of N-(p- carboxyphenyl)-5-ferrocenyl valeric acid amide represented by the formula:

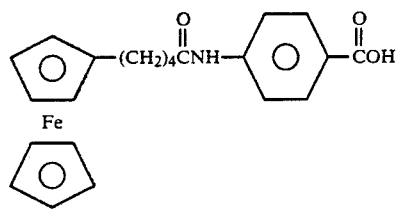

EXAMPLE 3

The procedure of Example 2 was repeated except that 10.9 g of N-(p-carboxyphenyl)-5-ferrocenyl valeric acid amide prepared in Preparation Example 3, 134.0 g of polyethylene glycol (average molecular weight : 600) and 2.0 ml of concentrated sulfuric acid were used.

Figure 3:
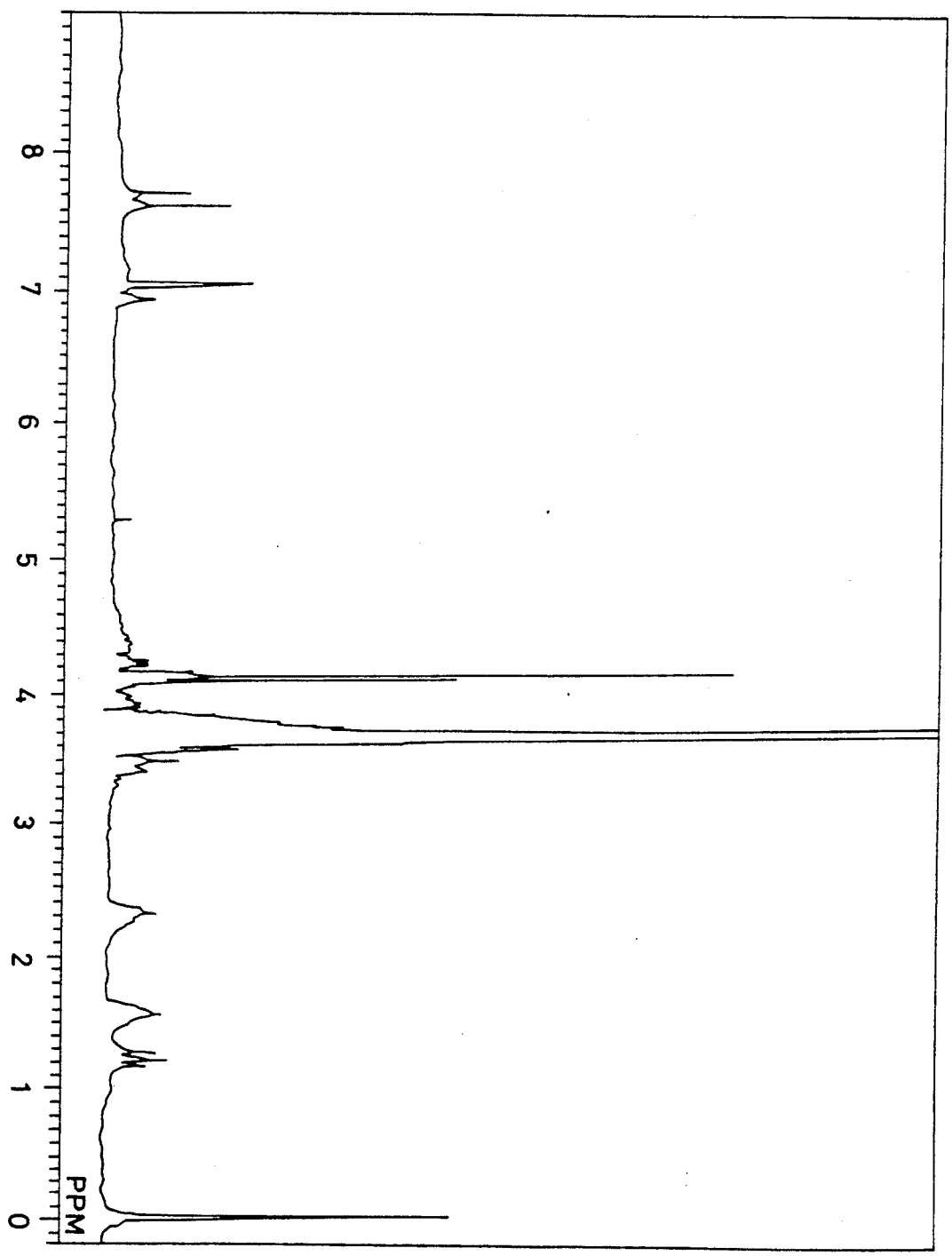

The amount of the resulting compound was 8.7 g, and the yield was 32%. Elemental analytical values of that substance were: carbon, 54.0%; hydrogen, 7.4%; nitrogen, 0.01%, and the results of measurement of proton nuclear magnetic resonance spectrum was as shown in FIG. 3.

These results show that the purified product was a ferrocene derivative having the following structure:

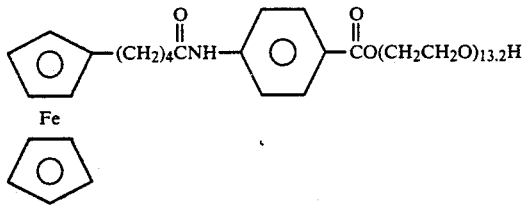

EXAMPLE 4

Into 100 cc of water, the ferrocene derivative obtained in Example 1 as a surfactant (micelle forming agent) was added to make 2 mM solution. Then 0.1 g of phthalocyanine was added to 20 cc of said solution and dispersed by stirring with supersonic waves for 10 minutes, to form a micelle. Further, after the mixture was stirred for two days and nights by a stirrer, the resulting micelle solution (dispersed solution) was subjected to centrifugal separation at 2,000 rpm for 30 minutes.

Figure 4:
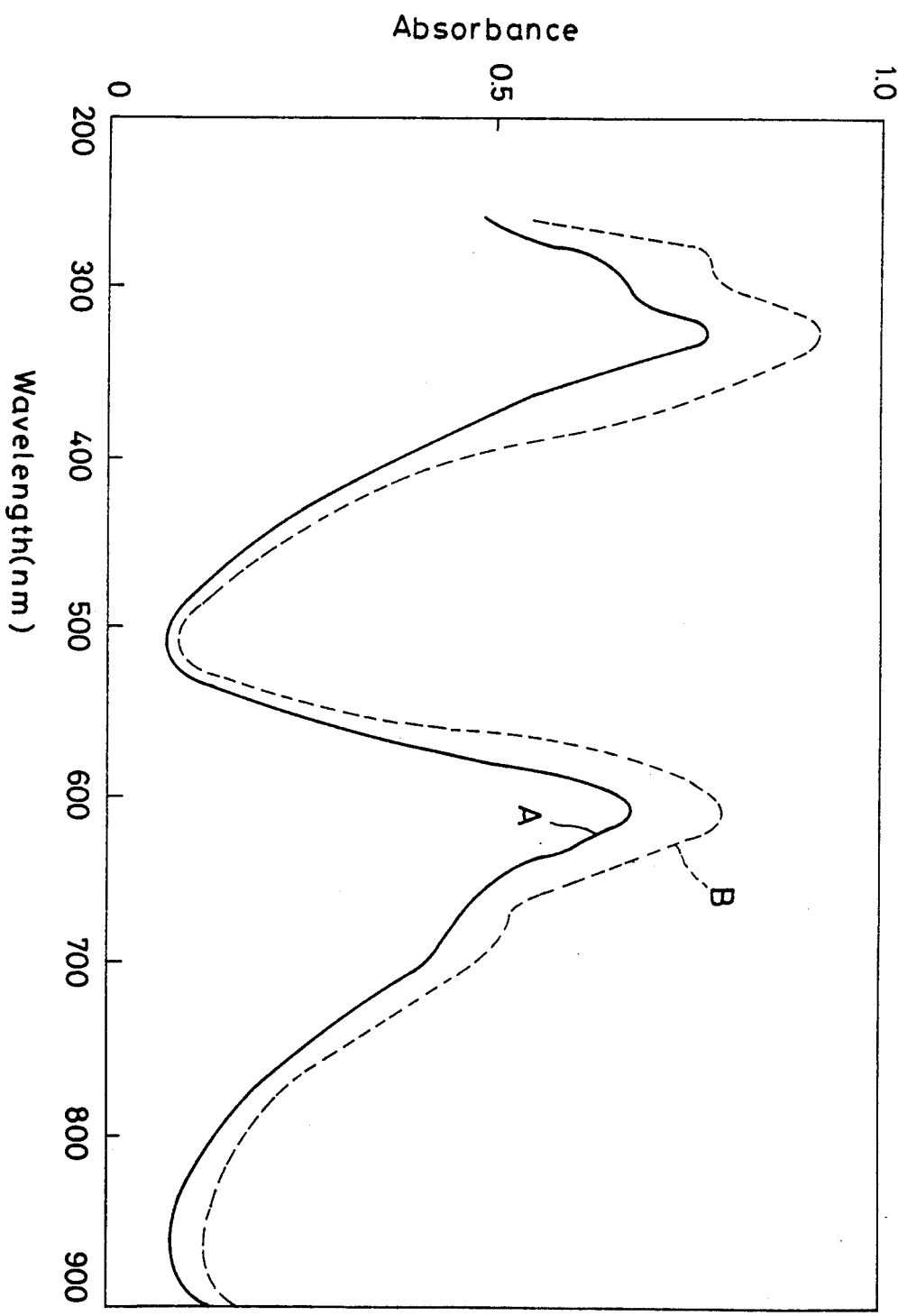
FIG. 4 shows a visible absorption spectrum of the supernatant obtained and a visible absorption spectrum of the thin film formed on ITO in Example 4.

A visible-absorption spectrum of the supernatant is shown in FIG. 4 (Mark A). This confirmed that phthalocyanine was soluble (dispersed) in the micelle solution. The solubility of phthalocyanine was 9.8 mM/2 mM micelle forming agent solution.

Into the above solution, lithium bromide as a supporting salt was added so that the concentration may be 0.1 M, and stirred for 10 minutes by the use of a stirrer.

With the use of this micelle solution as an electrolyte, ITO transparent glass electrode as the anode, platinum as the cathode and a saturated calomel electrode as a reference electrode, constant electric potential electrolysis was carried out at 25° C. at the applied voltage of 0.5 V and an electric current density of 12 $\mu A/cm^2$ for 30 minutes. The amount of electricity passed in that period was 0.02 coulomb (C).

As the result, a thin film of phthalocyanine was formed on the ITO transparent glass electrode. A visible absorption spectrum of phthalocyanine on the ITO transparent glass electrode is shown in FIG. 4 (Mark B). Since FIG. 4 (Mark A) agreed with FIG. 4 (Mark B), it was confirmed that the thin film on the ITO transparent glass electrode was phthalocyanine. An ultraviolet (UV) absorption spectrum showed that the thickness of the thin film was 1.1 $\mu m$.

Further, as the result of cyclic voltammetry, the oxidation-reduction potential was 0.213 V, and the difference between the peak potentials of oxidation and reduction was 95 mV, which shows that the efficiency of oxidation-reduction was improved compared with that in Comparative Example 1 to be mentioned later.

EXAMPLE 5

The ferrocene derivative obtained in Example 2 as a surfactant (micelle forming agent) was added into 100 cc of water to make 2 mM solution. Then 0.1 g of phthalocyanine was added to 20 cc of said solution, and dispersed by stirring for 10 minutes with supersonic waves to make a micelle. The mixture was further stirred for two days and nights with a stirrer, and then the micelle solution (dispersed solution) thus obtained was subjected to centrifugal separation at 2,000 rpm for 30 minutes.

Figure 5:
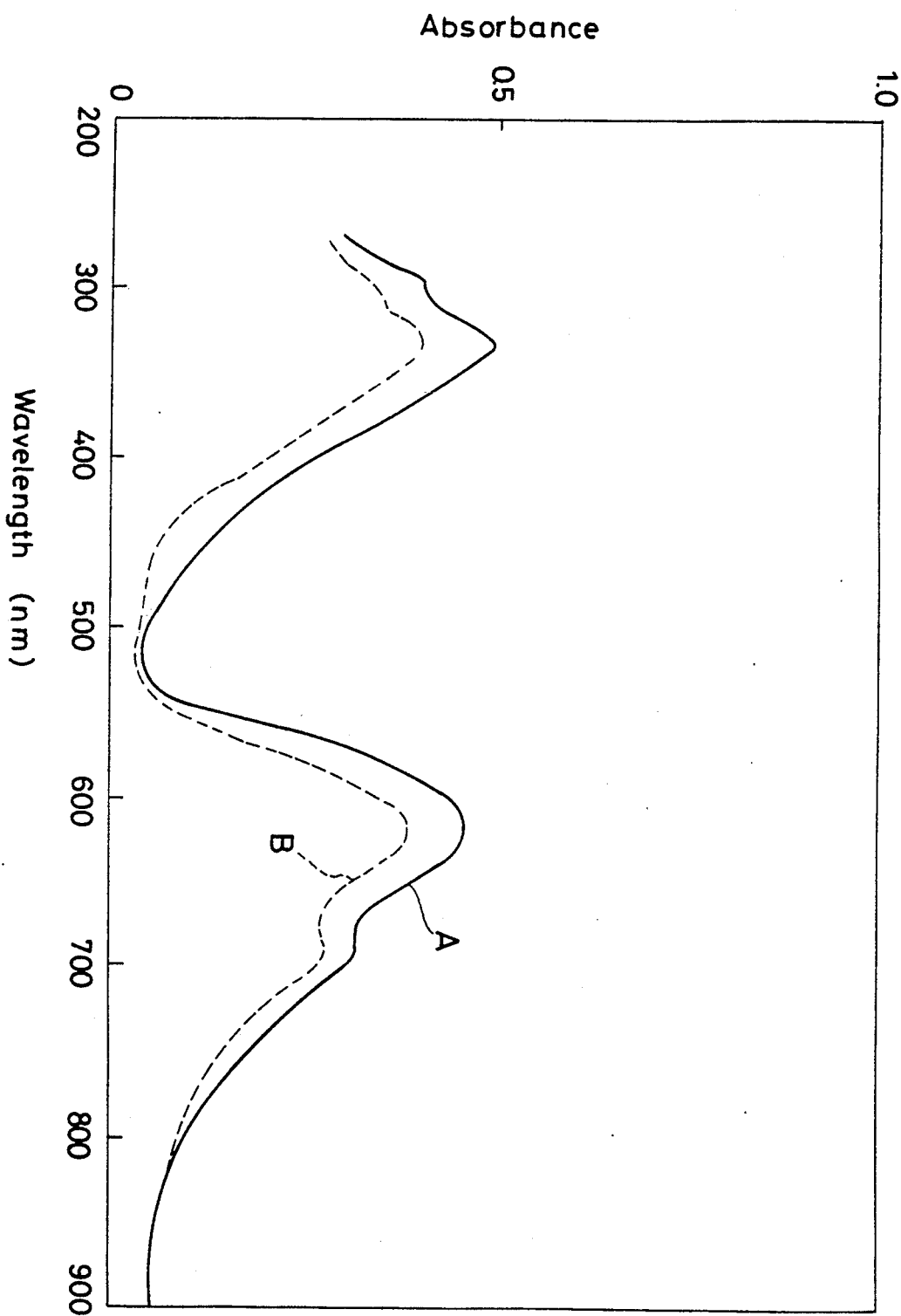
FIGS. 5 and 6 show visible absorption spectrums of the supernatant and of the thin film formed on ITO in Examples 5 and 6, respectively.

A visible absorption spectrum of the supernatant obtained is shown in FIG. 5 (Mark A). This confirmed that phthalocyanine was soluble (dispersed) in the micelle solution. The solubility of phthalocyanine was 7.2 mM/2 mM micelle forming agent solution.

Into this solution, lithium bromide as a supporting salt was added so that the concentration would be 0.1 M, and stirred for 10 minutes with a stirrer.

With the use of said solution as an electrolyte, an ITO transparent glass electrode as an anode, platinum as a cathode and a saturated calomel electrode as a reference electrode, constant electric potential electrolysis was carried out at 25° C. at the applied voltage of 0.5 V and an electric current density of 15 $\mu A/cm^2$ for 30 minutes. The amount of electricity passed in that period was 0.03 C.

As the result, a thin film of phthalocyanine was formed on the ITO transparent glass electrode. A visible absorption spectrum of phthalocyanine on the ITO transparent glass electrode is shown in FIG. 5 (Mark B). Since FIG. 5 (Mark A) agreed with FIG. 5 (Mark B), it was confirmed that the thin film on the ITO transparent glass electrode was phthalocyanine. A UV absorption spectrum showed that the thickness of the thin film was 0.7 $\mu m$.

Further, as the result of cyclic voltammetry, the oxidation-reduction potential was 0.205 V, and the difference between the peak potentials of oxidation and reduction was 85 mV, which shows that the efficiency of oxidation-reduction was improved compared with that in Comparative Example 1 to be mentioned later.

EXAMPLE 6

The ferrocene derivative obtained in Example 3 as a surfactant (micelle forming agent) was added into 100 cc of water to make 2 mM solution. Then 0.1 g of phthalocyanine was added to 20 cc of said solution and dispersed by stirring for 10 minutes with supersonic waves to form a micelle. The mixture was further stirred for two days and nights with a stirrer, and then the micelle solution (dispersed solution) thus obtained was subjected to centrifugal separation at 2,000 rpm for 30 minutes.

Figure 6:
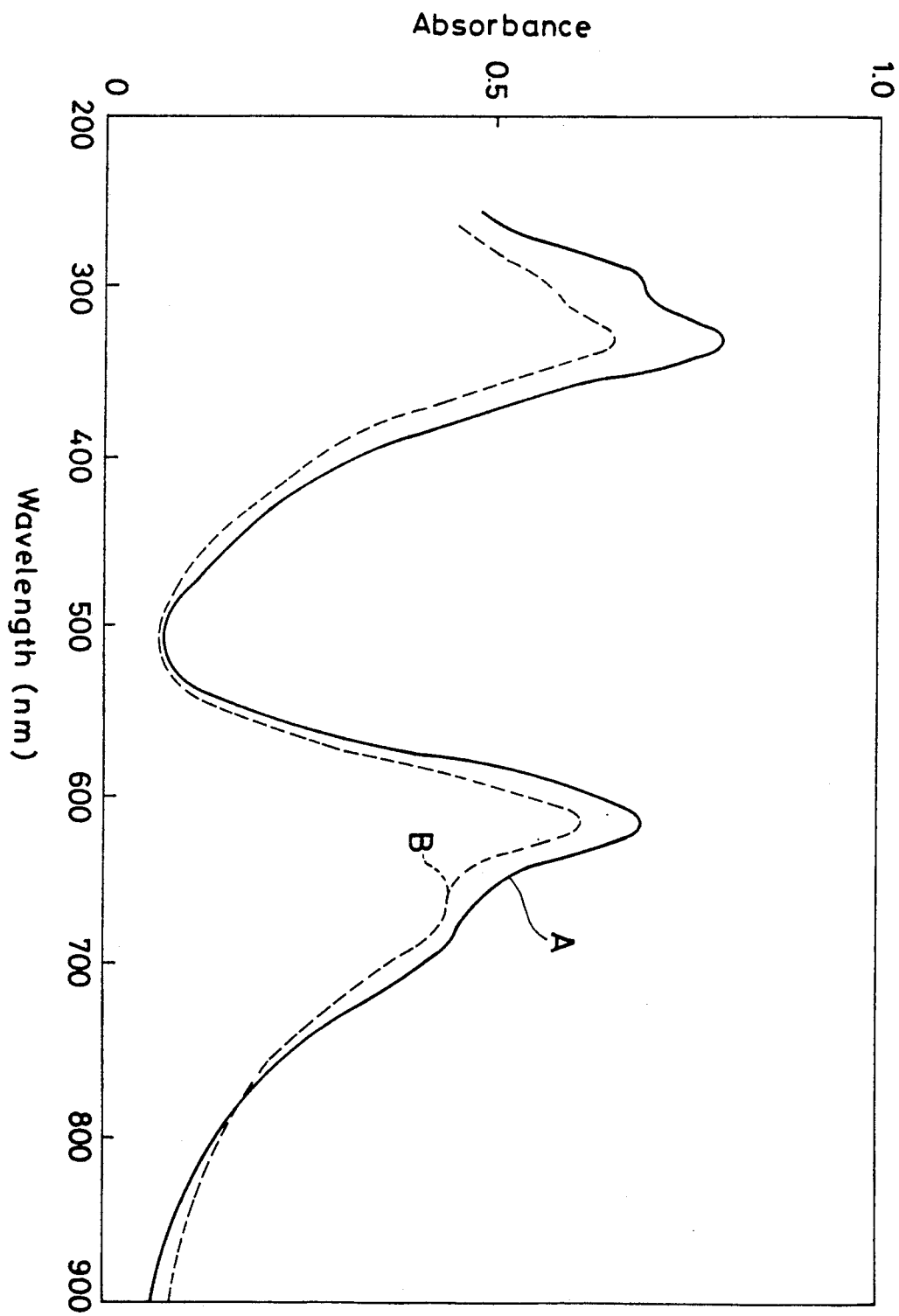

A visible absorption spectrum of the supernatant is shown in FIG. 6 (Mark A). This confirmed that phthalocyanine was soluble (dispersed) in the micelle solution. The solubility of phthalocyanine was 8.1 mM/2 mM micelle forming agent solution.

To this solution, lithium bromide as a supporting salt was added so that the concentration would be 0.1 M and stirred for 10 minutes with a stirrer.

With the use of the solution as an electrolyte, an ITO transparent glass electrode as an anode, platinum as an cathode and a saturated calomel electrode as a reference electrode, constant electric potential electrolysis was carried out at 25° C. at the applied voltage of 0.5 V, and an electric current density of 18 $\mu A/cm^2$ for 30 minutes. The amount of electricity passed in that period was 0.03 C.

As the result, a thin film of phthalocyanine was found on the ITO transparent glass electrode. A visible absorption spectrum of phthalocyanine on the ITO transparent glass electrode is shown in FIG. 6 (Mark B). Since FIG. 6 (Mark A) agreed with FIG. 6 (Mark B), it was confirmed that the thin film on the ITO transparent glass electrode was phthalocyanine. A UV absorption spectrum showed that the thickness of the thin film was 1.2 $\mu m$.

Further, as the result of cyclic voltammetry, the oxidation-reduction potential was 0.183 V, and the difference between the peak potentials of oxidation and reduction was 47 mV, which showed that the efficiency of oxidation-reduction was improved compared with that in Comparative Example 1 to be mentioned later.

PREPARATION EXAMPLE 4

(1) In the presence of 64.6 g of anhydrous aluminum chloride, 29.0 g of benzene bromide and 25.0 g of anhydrous glutaric acid were reacted at room temperature for 8 hours in a methylene chloride solvent. After completion of the reaction, the reaction mixture was subjected to methylene chloride extraction, alkali extraction and acid treatment while treated with dilute hydrochloric acid, to obtain 39.4 g of the compound (1) represented by the formula:

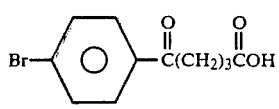

(2) In the presence of zinc amalgam prepared from 32.7 g of zinc and 13.6 g of mercuric chloride, 20.0 g of the above compound (1) was refluxed for 5 hours in a mixed solvent of concentrated hydrochlorice acid and 1,2-dimethoxyethane.

After completion of the reaction, the reaction mixture was repeatedly subjected to ether extraction, alkali extraction, and acid treatment to obtain 15.1 g of the compound (2) represented by the formula:

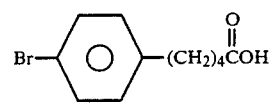

(3) An amount of 16.5 g of acid chloride of the compound (2) prepared from 15.0 g of the compound (2) and 50 ml of thionyl chloride, 10.6 g of anhydrous aluminum chloride, and 11.2 g of ferrocene were reacted at 5° C. for 4 hours in a methylene chloride solvent. After completion of the reaction, the reaction mixture was treated with dilute hydrochloric acid, then purified with silica gel column chromatography, to obtain 10.3 g of the compound (3) represented by the formula:

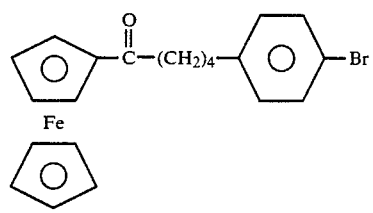

(4) In the presence of zinc amalgam prepared from 10.9 g of zinc and 4.5 g of mercuric chloride, 10.3 g of above compound (3) was refluxed for 5 hours in a mixed solvent of concentrated hydrochloric acid and ethanol.

After completion of the reaction, the reaction mixture was purified with silica gel column, to obtain 5.1 g of the compound (4) represented by the formula:

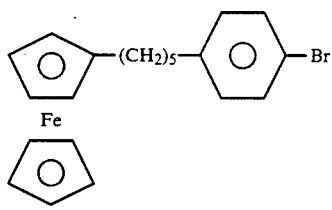

EXAMPLE 7

To 30.0 g of polyethylene glycol (average molecular weight, 600), 0.25 g of metallic sodium was added and stirred at 100° C. for one day and night. Then, 2.0 g of the above compound (4) 25 ml of $\gamma$-collidine and 0.5 g of copper (I) iodide were added thereto and reacted at 170° C. for 30 hours.

This reaction mixture was extracted with a mixture of equal amounts of water and n-butanol. The extract was washed with water and then was subjected to chromatographic purification by developing on a silica gel column using a mixture of ethyl acetate and methanol (ethyl acetate: methanol=4:1) as a solvent.

Figure 7:
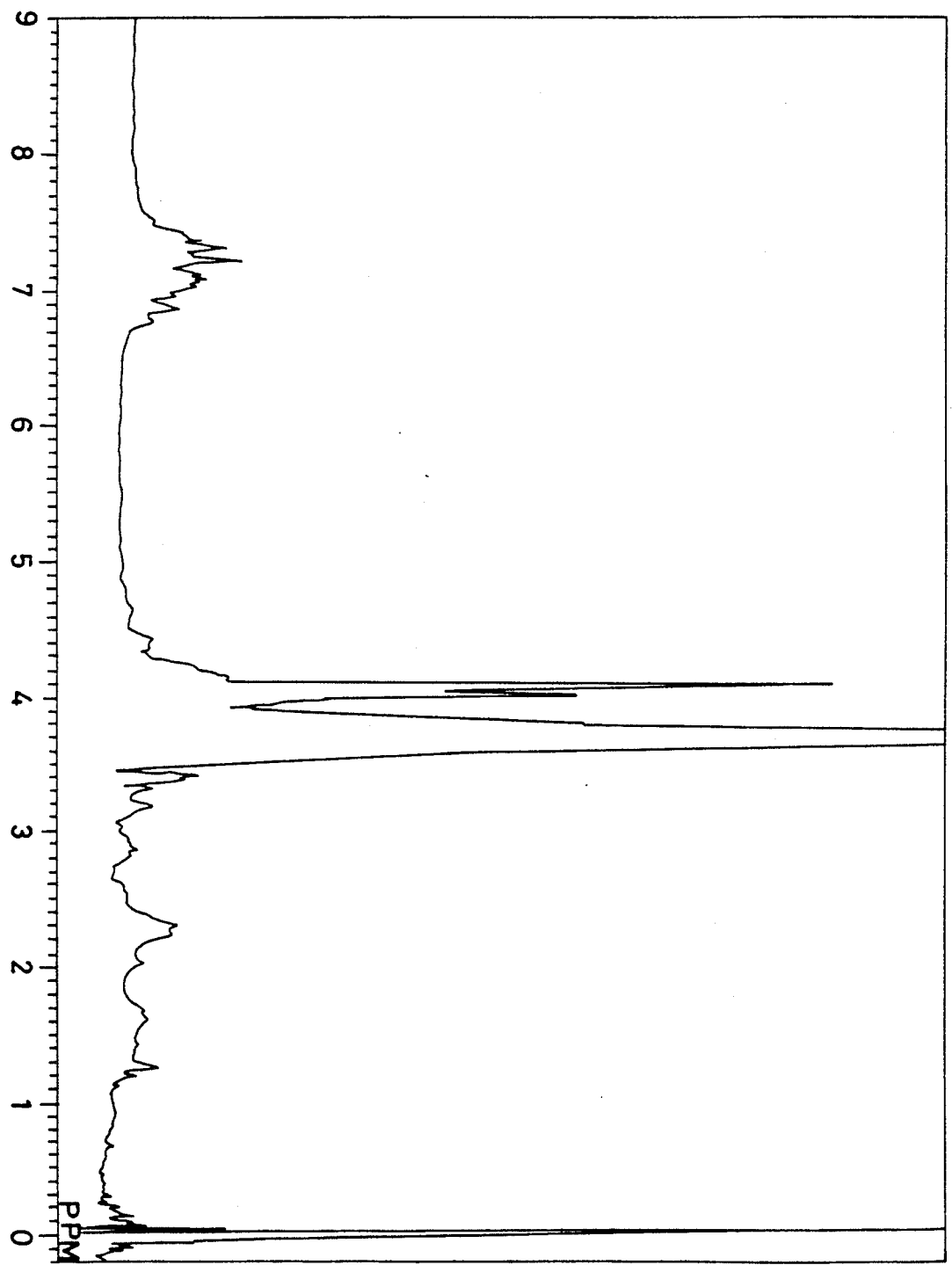
FIGS. 7 to 9 show a $^1$H-NMR spectrum of the ferrocene derivative obtained in Examples 7, 8 and 9, respectively.

For the purified product obtained after drying, the yield was 33% and the amount was 1.5 g. The elemental analytical values were : carbon, 61.5%; hydrogen, 9.0%. The results measuring proton nuclear magnetic resonance spectrum ($^1$H-NMR) were as shown in FIG. 7.

From the results above, it can be seen that the above purified product was a ferrocene derivative having the following structure:

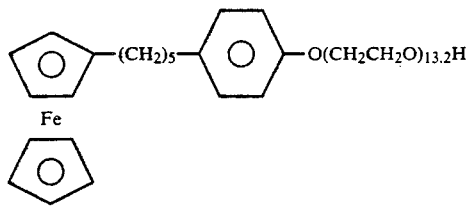

PREPARATION EXAMPLE 5

An amount of 3.0 g of compound (4) prepared in Preparation Example 4 (4) and 0.8 g of the copper (I) cyanide were heat-refluxed for 6 hours in a dimethyl formamide solvent. The hot mixture was treated with water, the resulting precipitate was treated with a warm aqueous solution of ethylenediamine. Then, a precipitate was extracted with benzene, washed with water, dried and concentrated.

The residue obtained and 1.3 g of potassium hydroxide were refluxed for 8 hours in a mixed solvent of ethanol and water. After completion of the reaction, the reaction mixture was treated with dilute hydrochloric acid, extracted with ethyl acetate, and then purified with a silica gel column chromatography to obtain 2.1 g of the following compound (5):

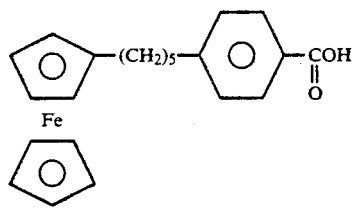

EXAMPLE 8

The procedure of Example 7 was repeated except that 34.0g of polyethylene glycol (average molecular weight, 600) and 0.5 cc of concentrated sulfuric acid were added to 2.1 g of the above compound (5) and reacted at 80° C. for 8 hours.

Figure 8:
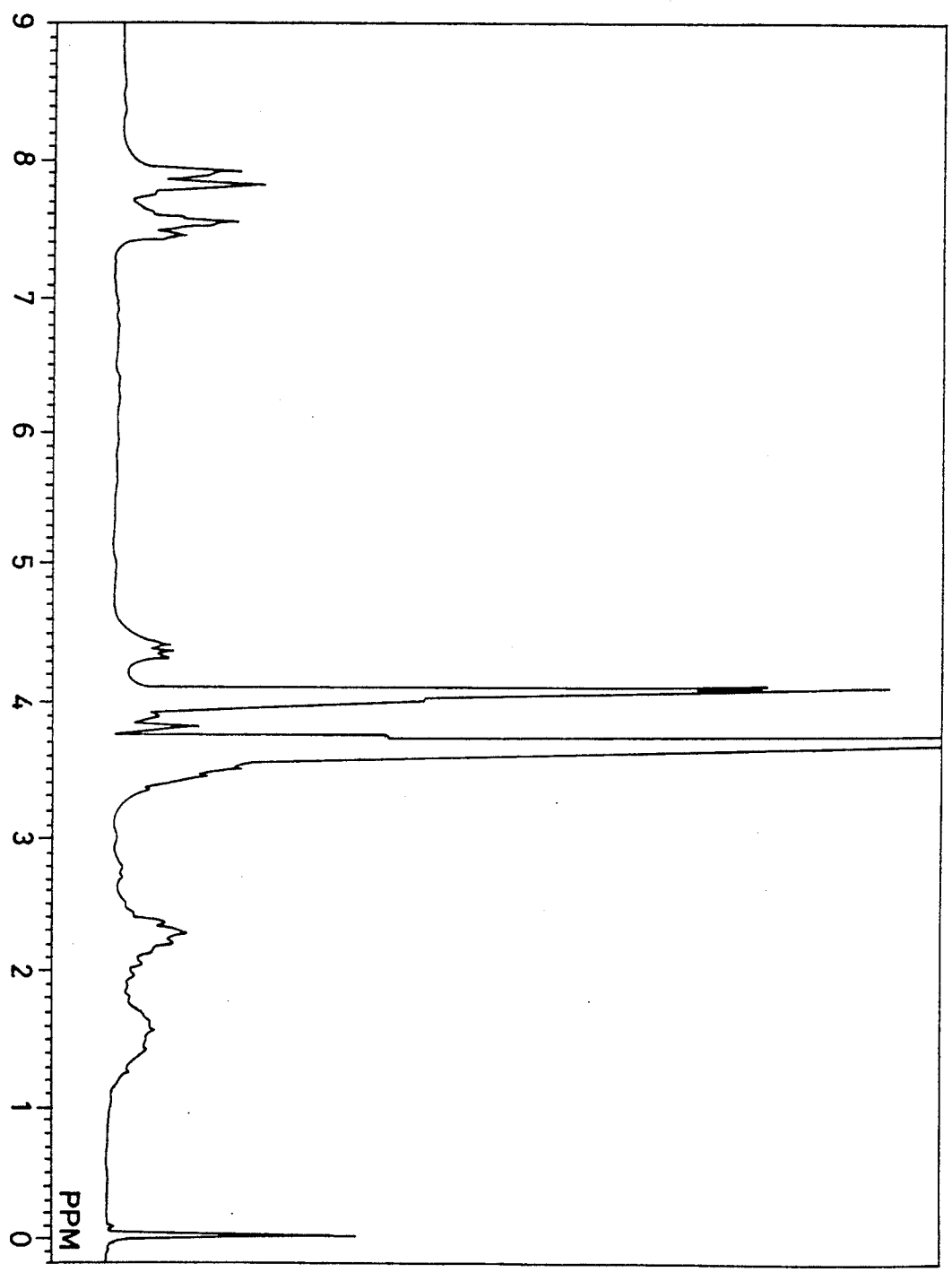

For the purified product obtained, the yield was 37% and the amount was 2.0 g. The elemental analytical values were: carbon, 60.9%; hydrogen, 7.9%. The results of measurement of $^1$H-NMR were as shown in FIG. 8.

From the above results, it can be seen that the above purified product was a ferrocene derivative having the following structure:

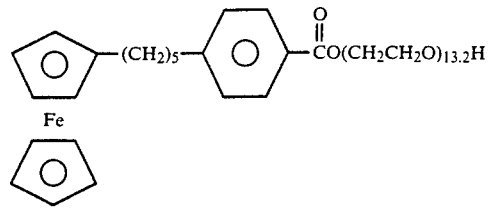

PREPARATION EXAMPLE 6

(1) In the presence of 21.6 g of anhydrous aluminum chloride, 25.1 g of ferrocene and 25.4 g of 4-bromo butyryl chloride were reacted at 5° C. for 2 hours in a methylene chloride solvent. After completion of the reaction, the reaction mixture was treated with dilute hydrochloric acid and then purified with a silica gel column to obtain 20.7 g of the following compound (6).

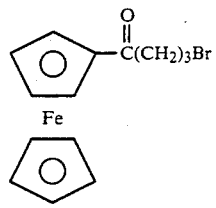

(2) In the presence of zinc amalgam prepared from 26.2 g of zinc and 10.9 g of mercuric chloride, 20.7 g of the above compound (6) was reacted at 80° C. for 3 hours in a mixed solvent of concentrated hydrochloric acid and ethanol. After completion of the reaction, the reaction mixture was extracted with ethyl acetate and purified with a silica gel column to obtain 6.1 g of the following compound (7):

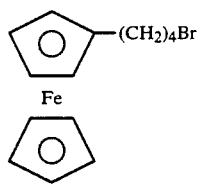

(3) In the presence of 0.3 g of tetra n-butyl ammonium fluoroborate, 2.7 g of the above compound (7) and 3.0 g of sodium azide were reacted at 100° C. for 7 hours in a water solvent. After completion of the reaction, the reaction mixture was extracted with ether and dried.

To the dried ether solution, 2.5 g of lithium aluminum hydride was added and refluxed for 5 hours and then treated with water to obtain 1.9 g of the following compound (8).

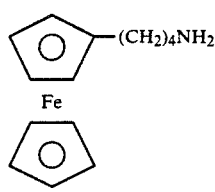

(4) In the presence of 1.4 g of triethylamine, 1.9 g of the following compound (8) and 1.5 g of terephthalic acid methylester chloride were reacted for 4 hours in a toluene solvent at room temperature. After completion of the reaction, the reaction mixture was treated with water, extracted with ethyl acetate and then purified with a silica gel column to obtain 2.6 g of the following compound (9).

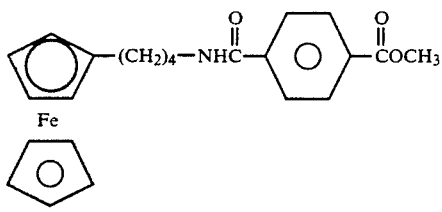
(9)

(5) An amount of 2.6 g of the above compound (9) and 0.7 g of potassium hydroxide were reacted at 50° C. for one hour in an ethanol solvent. After completion of the reaction, the reaction mixture was concentrated to obtain 2.3 g of the following compound (10).

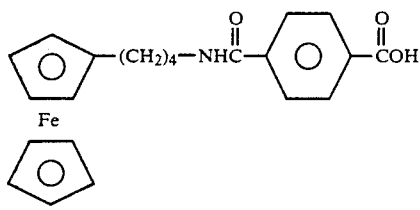
(10)

EXAMPLE 9

The procedure of Example 7 was repeated except that to 2.3 g of the above compound (10) 35 g of polyethylene glycol (average molecular weight, 600) and 0.5 cc of concentrated sulfuric acid were added and reacted at 90° C. for 8 hours.

For the purified product, the yield was 28% and the amount was 1.6 g. The elemental analytical values were: carbon, 59.4%; hydrogen, 7.4%; nitrogen, 1.3%.

Figure 9:
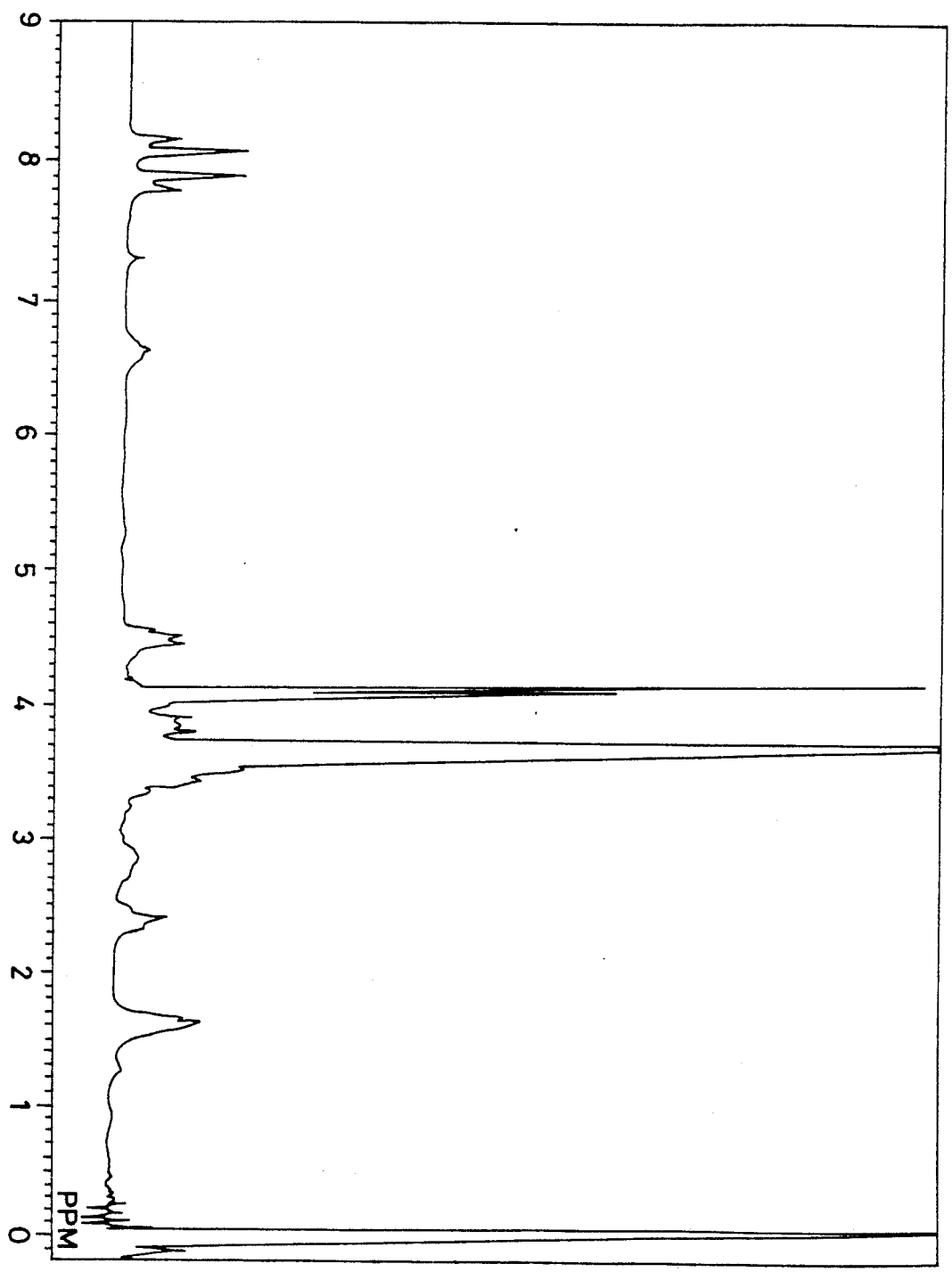

The results of the measurement of $^1$H-NMR were as shown in FIG. 9.

From the above purified results, it can be seen that the above purified product was a ferrocene derivative having the following structure:

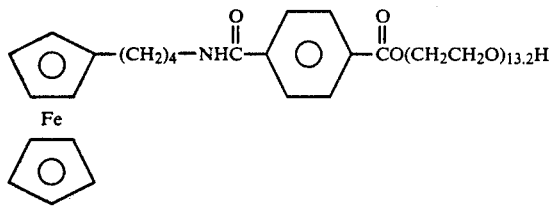

EXAMPLE 10

Into 100 cc of water was added a micelle forming agent composed of ferrocene derivative obtained in Example 7 to make a 2 mM solution. To 20 cc of the resulting micelle solution, 0.1 g of phthalocyanine (produced by Tokyo Kasei) was added and stirred by ultrasonic waves for 10 minutes to disperse and dissolve, followed by stirring for 2 days and nights with a stirrer.

Then, the dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 8.4 mM/2 mM micelle forming agent.

Into the dispersed and soluble micelle solution, lithium bromide was added so that the concentration became 0.1 M, and was stirred with a stirrer for 10 minutes. By using this solution as an electrolyte, an ITO transparent glass electrode as the anode, platinum as the cathode and a saturated calomel electrode as the reference electrode, constant potential electrolysis was carried out at 25° C. at the applied voltage of 0.5 V and an electric current density of 8.6 $\mu$A/cm$^2$ for 30 minutes. The amount of electric current passed in that period was 0.015 C.

As a result, a thin film of phthalocyanine was formed on the ITO transparent glass electrode.

Since the absorption spectrum on the ITO transparent glass electrode agreed with that of the dispersed and soluble micelle solution, it can be seen that the thin film on the ITO transparent electrode was phthalocyanine and the thickness of the film was 1.8 $\mu$m from the absorbance.

Into the micelle solution, lithium bromide was added as a supporting salt so that the concentration became 0.1 M. As the result of cyclic voltammetry, the oxidation-reduction potential was 0.226 V, and the difference between the peak voltage of oxidation and reduction was 117 mV, which shows that the efficiency of oxidation-reduction was improved compared with that in Comparative Example 1 to be mentioned later.

EXAMPLE 11

Into 100 cc of water was added a micelle forming agent composed of the ferrocene derivative obtained in Example 8 to make a 2 mM solution. To 20 cc of the resulting micelle solution, 0.1 g of phthalocyanine (produced by Tokyo Kasei) was added and stirred by ultrasonic wave for 10 minutes to disperse and dissolve, followed by stirring for 2 days and nights with a stirrer.

Then, the dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 8.2 mM/2 mM micelle forming agent.

Into the dispersed and soluble micelle solution, lithium bromide was added so that the concentration became 0.1 M, and was stirred with a stirrer for 10 minutes. By using this solution as an electrolyte, an ITO transparent glass electrode as the anode, platinum as the cathode and a saturated calomel electrode as the reference electrode, constant potential electrolysis was carried out at 25° C. at the applied voltage of 0.5 V and an electric current density of 11.2 $\mu$A/cm$^2$ for 30 minutes. The amount of electric current passed in that period was 0.02 C.

As a result, a thin film of phthalocyanine was formed on the ITO transparent glass electrode.

Since the absorption spectrum on the ITO transparent glass electrode agreed with that of the dispersed and soluble micelle solution, it can be seen that the thin film on the ITO transparent electrode was phthalocyanine and the thickness of the film was 2.5 ||m from the absorbance.

EXAMPLE 12

Into 100 cc of water was added a micelle forming agent composed of the ferrocene derivative obtained in Example 9 to make 2 mM solution. To 20 cc of the resulting micelle solution, 0.1 g of phthalocyanine (produced by Tokyo Kasei) was added and stirred by ultrasonic wave for 10 minutes to disperse and dissolve, followed by stirring for 2 days and nights with a stirrer. Then, the dispersed and soluble micelle solution was subjected to centrifugal separation for 30 minutes at 2000 rpm.

A visible absorption spectrum of the supernatant confirmed that phthalocyanine was dispersed. Its absorbance shows that the solubility of phthalocyanine was 8.5 mM/2 mM micelle forming agent.

Into the dispersed and soluble micelle solution, lithium bromide was added so that the concentration became 0.1 M, and was stirred with a stirrer for 10 minutes. By using this solution as an electrolyte, an ITO transparent glass electrode as the anode, platinum as the cathode and a saturated calomel electrode as the reference electrode, controlled potential electrolysis was carried out at 25° C. at the applied voltage of 0.5 V and an electric current density of 13.1 $\mu$A/cm$^2$ for 30 minutes. The amount of electric current passed in that period was 0.02 C.

As a result, a thin film of phthalocyanine was formed on the ITO transparent glass electrode.

Since the absorption spectrum on the ITO transparent glass electrode agreed with that of the dispersed and soluble micelle solution, it can be seen that the thin film on the ITO transparent electrode was phthalocyanine and the thickness of the film was 2.6 $\mu$m from the absorbance.

COMPARATIVE EXAMPLE 1

Into 100 cc of water was added the compound (FPEG), represented by the formula:

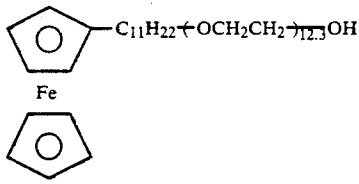

as a surfactant (micelle forming agent) to make a 2 mM solution. To 20 cc of the resulting micelle solution, 0.1 g of phthalocyanine was added and stirred by ultrasonic wave for 10 minutes to disperse and dissolve, followed by stirring for 2 days and nights with a stirrer. Then, the micelle solution (dispersed solution) was subjected to centrifugal separation for 30 minutes at 2000 rpm.

A visible absorption spectrum of the supernatant confirmed that phthalocyanine was soluble (dispersed) in the micelle solution. The solubility of phthalocyanine was 4.1 mM/2 mM micelle forming agent.

Into this solution, lithium bromide was added as a supporting salt so that the concentration became 0.1 M, and was stirred with a stirrer for 10 minutes.

By using this solution as an electrolyte, an ITO transparent glass electrode as the anode, platinum as the cathode and a saturated calomel electrode as the reference electrode, constant potential electrolysis was carried out at 25° C. at the applied voltage of 0.5 V and an electric current density of 17.2 $\mu$A/cm$^2$ for 30 minutes. The amount of electric current passed in that period was 0.07 C.

As a result, a thin film of phthalocyanine was formed on the ITO transparent glass electrode. It can be seen that the thickness of the thin film of phthalocyanine was 1.0 $\mu$m from the UV absorption spectrum.

As the result of cyclic voltammetry, the oxidation reduction potential was 0.260 V, and the difference between the peak voltage of oxidation and reduction was 70 mV.

PREPARATION EXAMPLE 7

(1) In the presence of 14.6 g of anhydrous aluminum chloride, 9.4 g of ferrocene and 10.0 g of 2-phenyl glutaric anhydride were reacted for 2 hours at room temperature in a methylene chloride solvent.

After completion of the reaction, the reaction mixture was treated with dilute hydrochloric acid and then extracted with methylene chloride, with alkali, treated with acid to obtain 16.6 g of the isomer mixture of the following compound (11) and (12) (yield, 86%).

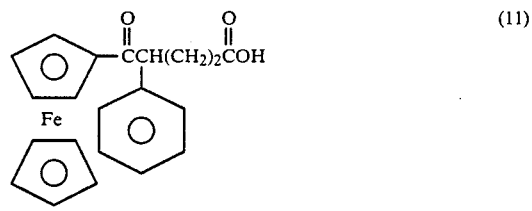

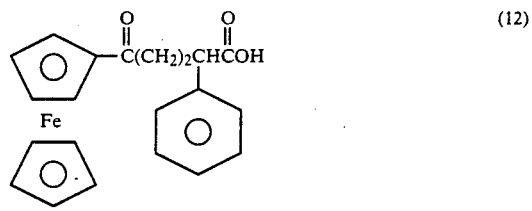

(2) In the presence of zinc amalgam prepared from 9.6 g of zinc and 4.4 g of mercuric chloride, 8.3 g of the mixture of the compounds (11) and (12) were reacted at 80° C. for 2 hours in a mixed solvent of concentrated sulfuric acid and 1,2-dimethoxy ethane.

After completion of the reaction, the reaction mixture was extracted with ethyl acetate and purified with a silica gel column to obtain 3.9 g of the isomer mixture of the following compounds (13) and (14) (yield, 49%).

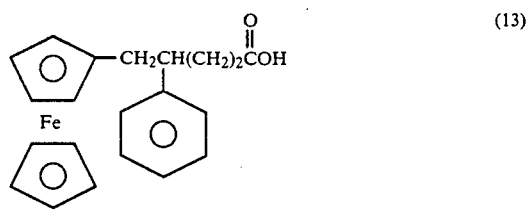

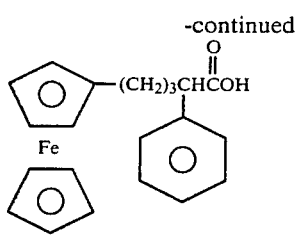
(14)

EXAMPLE 13

To 3.9 g of the isomer mixture of the compounds (13) and (14) obtained in Preparation Example 7, 66 g of polyethylene glycol (average molecular weight, 600) and 0.5 ml of concentrated sulfuric acid were added and reacted at 80° C. for 8 hours.

The reaction mixture was extracted with a mixture of equal amounts of water and n-butanol. The extract was washed with water and then was subjected to chromatographic purification by developing on a silica gel column using a mixture of ethyl acetate and methanol (4:1) as a developing solvent.

Figure 10:
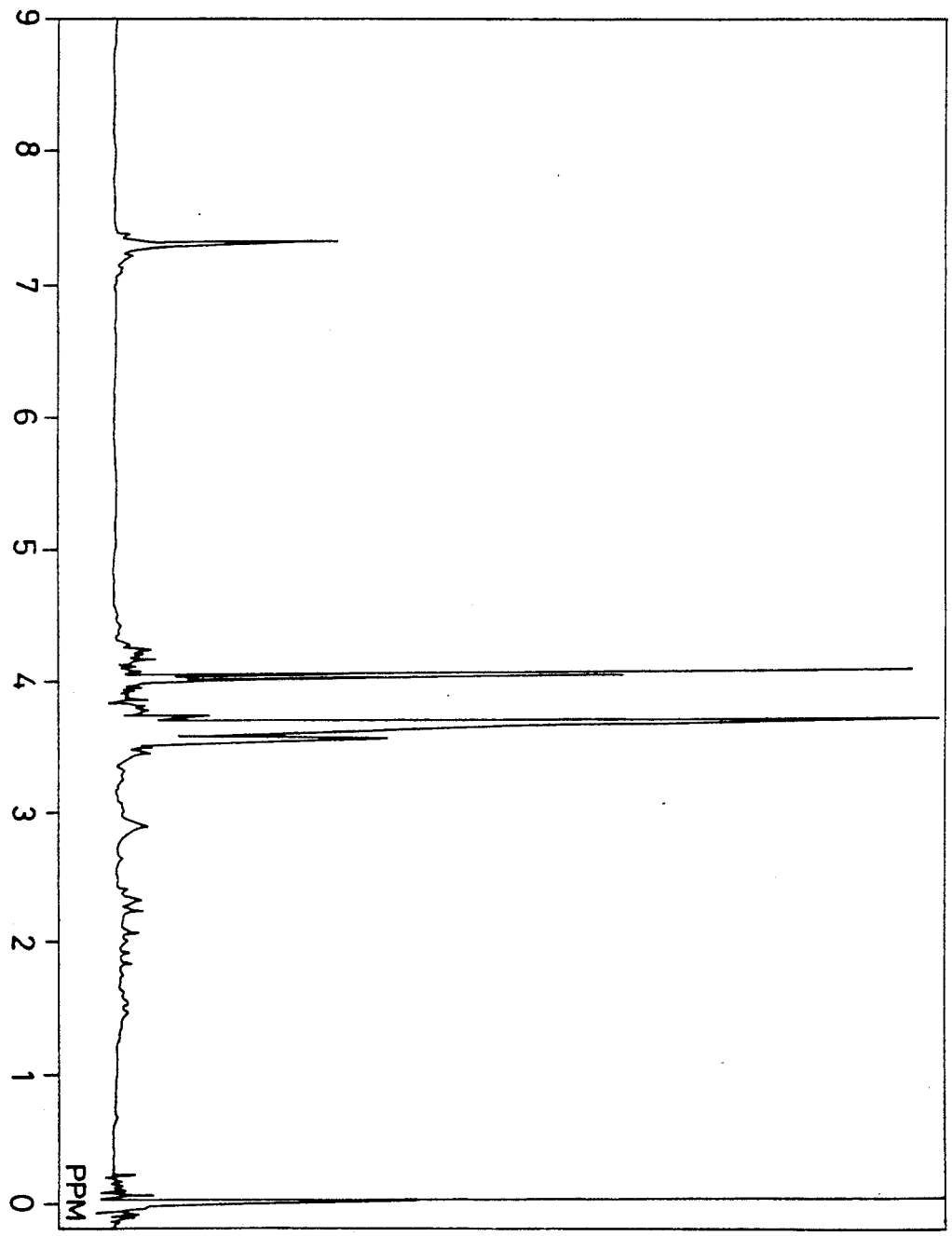
FIG. 10 shows a $^1$H-NMR of the ferrocene derivative obtained in Example 13.

For the purified product obtained after drying, the amount was 3.5 g (yield, 34%). The elemental analytical values were: carbon, 61.0%; hydrogen, 8.2%. The results of the measurement of $^1$H-NMR were as shown in FIG. 10.

From the above results, it was identified that the above purified product was a ferrocene derivative having the following structure (isomer).

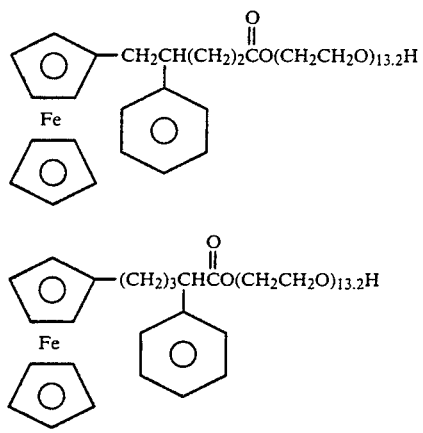

EXAMPLE 14

Into 100 cc of water was added ferrocene derivative obtained in Example 13 to make a 2 mM solution. To 20 cc of the resulting micelle solution, 0.1 g of phthalocyanine (produced by Tokyo Kaeei) was added and stirred by ultrasonic wave for 10 minutes to disperse and dissolve, followed by stirring for 2 days and nights with a stirrer. Then, the dispersed and soluble micelle solution was subjected to centrifugal separation for 30 minutes at 2000 rpm. A visible absorption spectrum of the supernatant confirmed that phthalocyanine was dispersed. Its absorbance shows that the solubility of the micelle forming agent was 8.4 mM/2 mM micelle forming agent.

Into dispersed and soluble micelle solution, lithium bromide was added so that the concentration became 0.1 M, and was stirred with a stirrer for 10 minutes. By using this solution as an electrolyte, an ITO transparent glass electrode as the anode, platinum as the cathode and a saturated calomel electrode as the reference electrode, constant potential electrolysis was carried out at 25° C. at the applied voltage of 0.5 V and an electric current density of 9.8 μA/cm$^2$ for 30 minutes. The amount of electric current passed in that period was 0.015 C.

As a result, a thin film of phthalocyanine was formed on the ITO transparent glass electrode. Since the absorption spectrum on the ITO transparent glass electrode agreed with that of the dispersed and soluble micelle solution, it can be seen that the thin film on the ITO transparent glass electrode was phthalocyanine and the thickness of the film was 2.2 μm from the absorbance.

Again, the to micelle solution, lithium bromide was added as a supporting salt so that the concentration became 0.1 M. As the result of cyclic voltammetry, the oxidation-reduction potential was 0.192 V, and the difference between the peak voltage of oxidation and reduction was 60 mV.

PREPARATION EXAMPLE 8

(1) In the presence of 1 cc of sulfuric acid, 8.0 g of the mixture of the compounds (11) and (12) obtained in Preparation Example 7 (1) was refluxed for 5 hours in an ethanol solvent. After completion of the reaction, the reaction mixture was concentrated, treated with alkali, extracted with ether and after drying, the resulting ether was distilled away to obtain 8.1 g of isomer mixture of the following compounds (15) and (16).

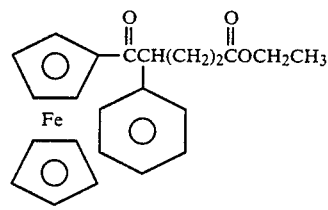
(15)

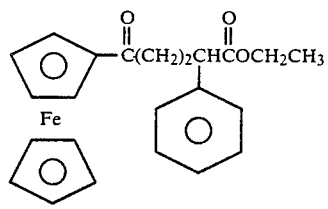
(16)

(2) An amount of 8.1 g of the mixture of the compounds (15) and (16) obtained in (1) above, 8.0 g of anhydrous aluminum chloride and 3.8 g of sodium borohydride were refluxed for 2 hours in a tetrahydrofuran solvent. After completion of the reaction, the reaction mixture was treated with dilute hydrochloric acid and extracted with ethyl acetate and then purified with a silica gel column to obtain 4.2 g of the isomer mixture of the following compounds (17) and (18) (yield, 60%).

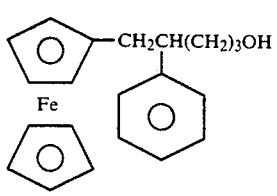
(17)

-continued

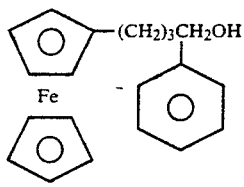 (18)

(3) An amount of 4.2 g of the mixture of the compounds (17) and (18) obtained in (2) above, 4.7 g of triphenylphosphine and 6.0 g of carbon tetrabromide were refluxed for 3 hours in a chloroform solvent. After completion of the reaction, the reaction mixture was concentrated, extracted with n-pentane and purified with a silica gel column to obtain 3.4 g of the isomer mixture of the following compounds (19) and (20) (yield, 69%).

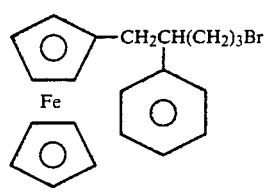 (19)

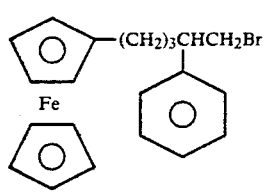 (20)

EXAMPLE 15

Into 42 g of polyethylene glycol (average molecular weight, 1000), 0.30 g of metallic sodium was added and stirred at 80° C. for one day and night. Then, 3.3 g of isomer mixture of the compounds (19) and (20) obtained in Preparation Example 8 (3) was added thereto and reacted at 110° C. for 10 hours. The reaction mixture was extracted with a mixture of equal amounts of water and n-butal. The extract was washed with water and then was subjected to chromatographic purification by developing on a silica gel column using a mixture of ethyl acetate and methanol (4:1) as a developing solvent.

Figure 11:
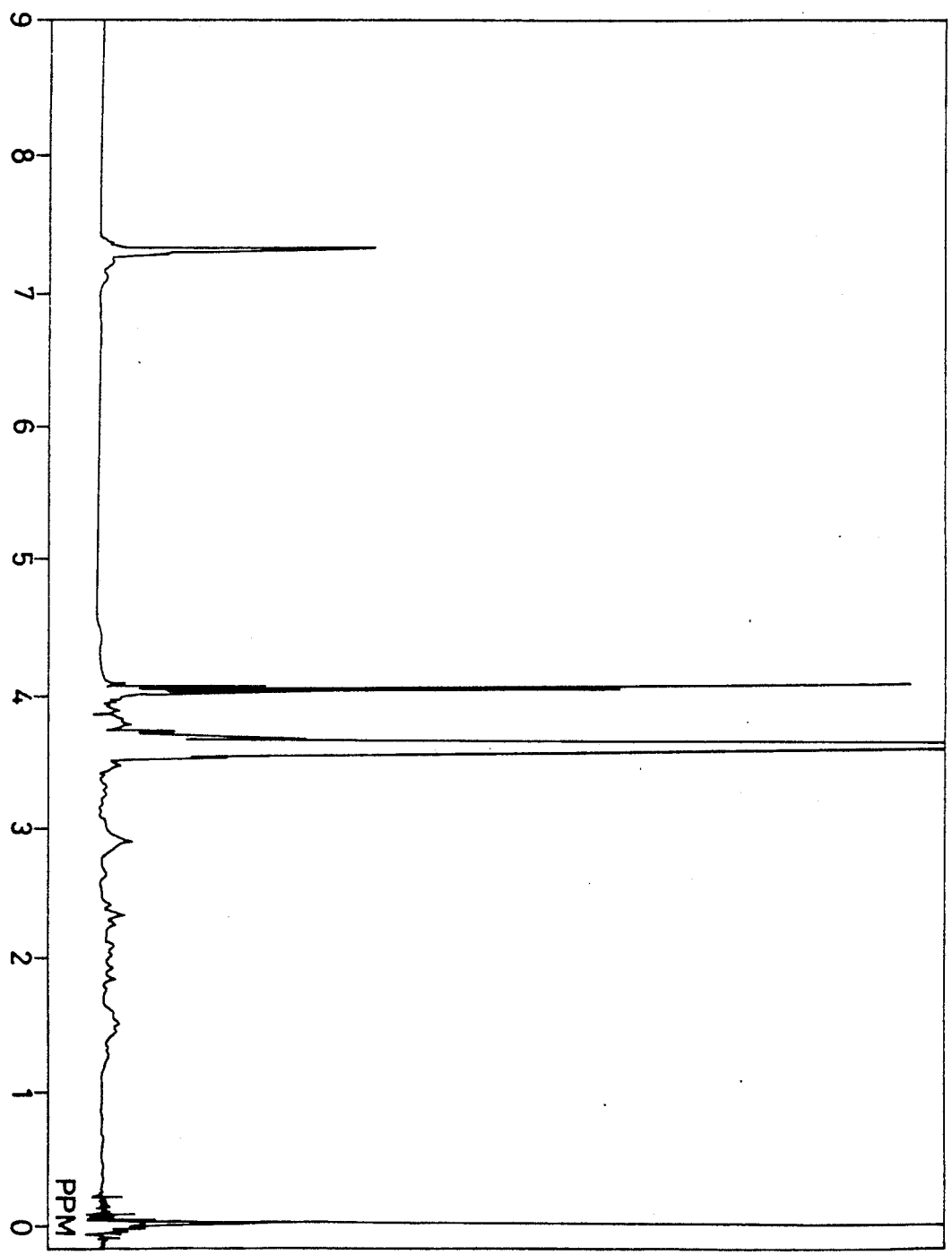
FIG. 11 shows a $^1$H-NMR of the ferrocene derivative obtained in Example 15.

For the purified product obtained, the amount was 3.9 g (yield, 37%), and the elemental analytical values were: carbon, 58.5%; hydrogen, 8.1%. The results of the measurement of $^1$H-NMR were as shown in FIG. 11.

From the above results, it was identified that the above purified product was a ferrocene derivative having the following structure (isomer).

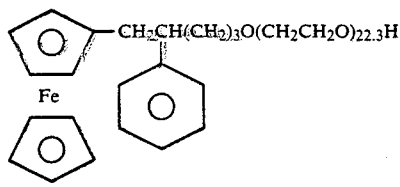

-continued

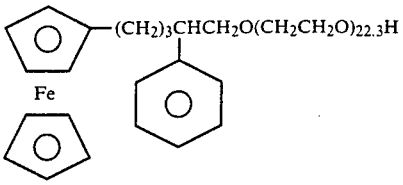

EXAMPLE 16

Into 100 cc of water was added the ferrocene derivative obtained in Example 15 to make a 2 mM solution. To 20 cc of the resulting micelle solution, 0.1 g of phthalocyanine (produced by Tokyo Kasei) was added and stirred by ultrasonic wave for 10 minutes to dissolve, followed by stirring for 2 days and nights with a stirrer. Then, the dispersed and soluble micelle solution was subjected to centrifugal separation for 30 minutes at 2000 rpm. A visible absorption spectrum of the supernatant confirmed that phthalocyanine was dispersed. Its absorbance shows that the solubility of the micelle forming agent was 7.9 mM/2 mM micelle forming agent.

Into dispersed and soluble micelle solution, lithium bromide was added so that the concentration became 0.1 M, and was stirred with a stirrer for 10 minutes.

By using this solution as an electrolyte, an ITO transparent glass electrode as the anode, platinum as the cathode and a saturated calomel electrode as the reference electrode, constant potential electrolysis was carried out at the applied voltage of 0.5 V and an electric current density of 9.4 $\mu$A/cm$^2$ for 30 minutes. The amount of electric current passed in that period was 0.02 C.

As a result, a thin film of phthalocyanine was formed on the ITO transparent glass electrode. Since the absorption spectrum on the ITO transparent glass electrode agreed with that of the dispersed and soluble micelle solution, it can be seen that the thin film on the ITO transparent electrode was phthalocyanine and the thickness of the film was 1.9 $\mu$m from the absorbance.

Again into micelle solution lithium bromide was added as a supporting salt so that the concentration became 0.1 M. As the result of cyclic voltammetry, the oxidation-reduction potential was 0.189 V, and the difference between the peak voltage of oxidation and reduction was 55 mV.

What is claimed is:

1. A ferrocene compound represented by the formula:

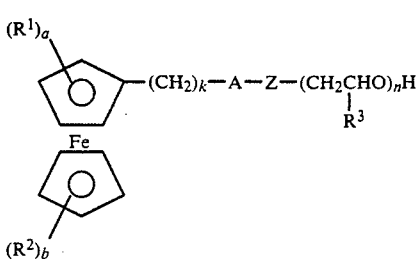

wherein A indicates

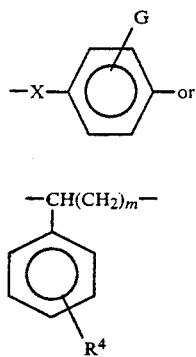

wherein X is —CH$_2$—, —O—,

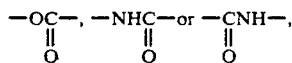

G is a hydrogen atom, a methyl group, or an ethyl group, R$^4$ is a hydrogen atom, a methyl group or an ethyl group, and m is a positive integer satisfying the expression $0 \leq k+m \leq 10$, Z is —O— or

and R$^1$ and R$^2$ are identical or different and each is H, NH$_2$, N(CH$_3$)$_2$, CH$_3$, CH$_3$O, OH or a halogen atom, and R$^3$ is a hydrogen atom or a methyl group, k is a positive integer satisfying the expression $0 \leq k+m \leq 10$, and n is a real number of 2 to 70, a is an integer of 1 to 4, and b is an integer of 1 to 5.

2. The ferrocene compound as claimed in claim 1, represented by the formula:

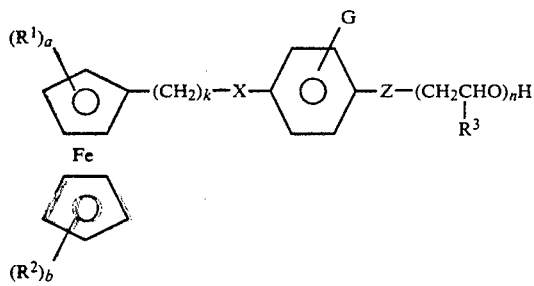

wherein k is a positive integer satisfying $0 \leq k \leq 10$ and m=0.

3. The ferrocene compound as claimed in claim 1, represented by the formula:

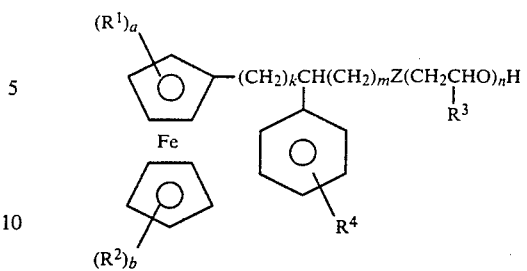

4. The ferrocene compound as claimed in claim 1, wherein R$^1$ and R$^2$ are identical or different and each is a halogen atom selected from the group consisting of chlorine, bromine and fluorine.

5. The ferrocene compound as claimed in claim 1, wherein k is 1 to 5.

6. The ferrocene compound as claimed in claim 1, wherein m is 1 to 5.

7. The ferrocene compound as claimed in claim 1, wherein the compound is of the formula

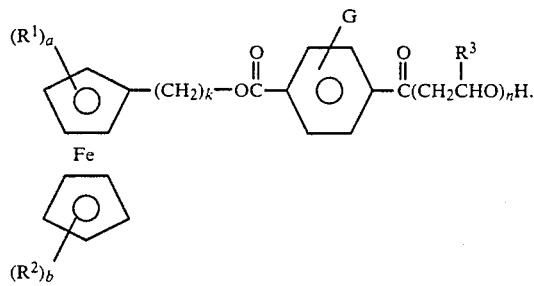

8. The ferrocene compound as claimed in claim 1, wherein the compound is of the formula

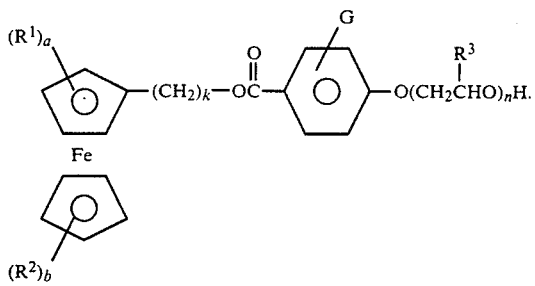

9. The ferrocene compound as claimed in claim 1, wherein the compound is of the formula

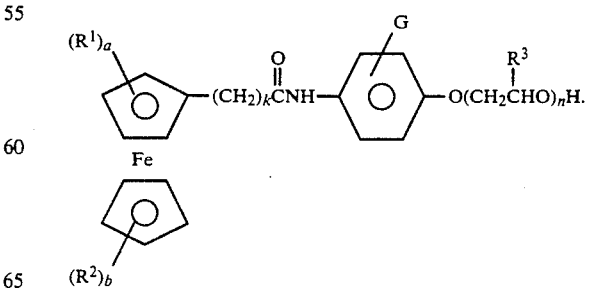

10. The ferrocene compound as claimed in claim 1, wherein the compound is of the formula 11. The ferrocene compound as claimed in claim 1, wherein the compound is of the formula

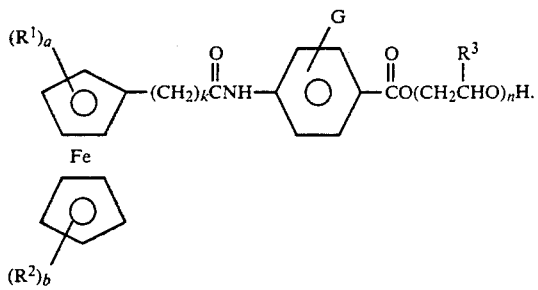

12. The ferrocene compound as claimed in claim 1, wherein the compound is of the formula

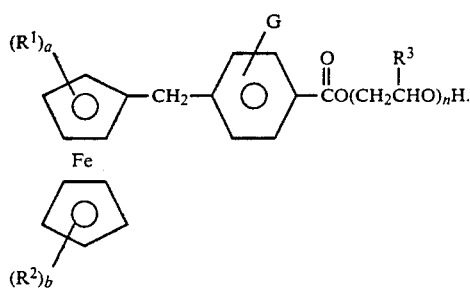

13. The ferrocene compound as claimed in claim 1, wherein the compound is of the formula

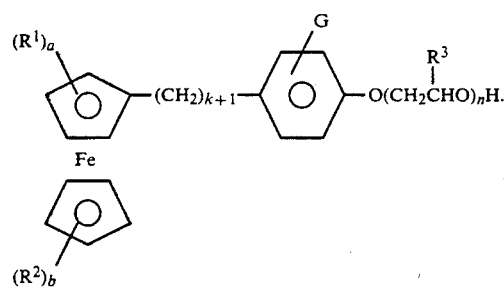

14. The ferrocene compound as claimed in claim 1, wherein the compound is of the formula

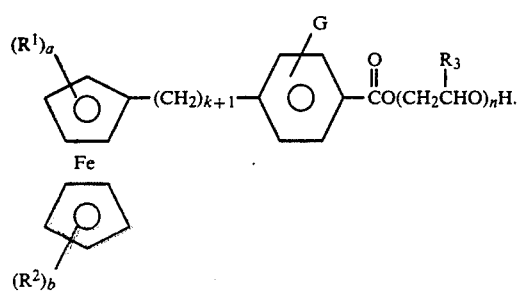

15. The ferrocene compound as claimed in claim 1, wherein the compound is of the formula

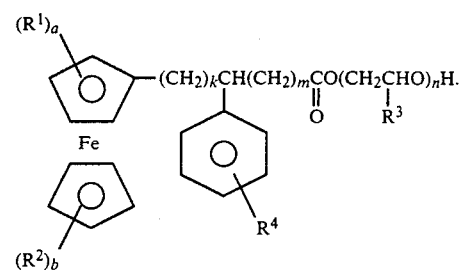

16. The ferrocene compound as claimed in claim 1, wherein the compound is of the formula

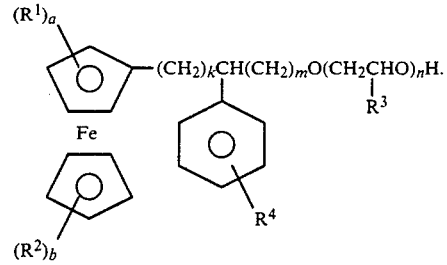

17. The ferrocene compound as claimed in claim 1, wherein the compound is of the formula

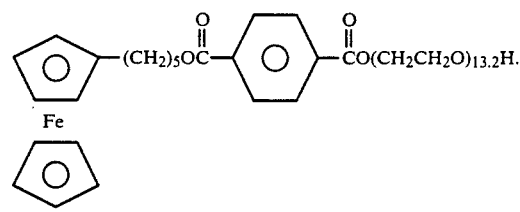

18. The ferrocene compound as claimed in claim 1, wherein the compound is of the formula

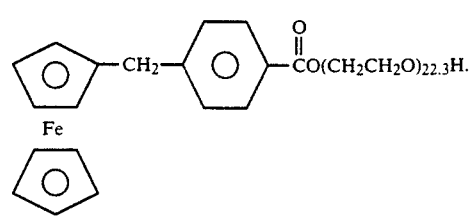

19. The ferrocene compound as claimed in claim 1, wherein the compound is of the formula

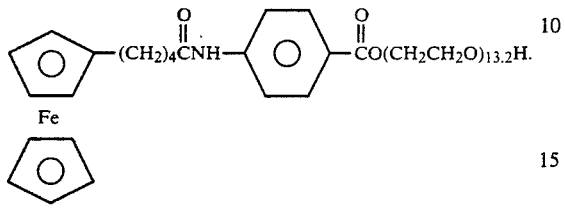

20. The ferrocene compound as claimed in claim 1, wherein the compound is of the formula

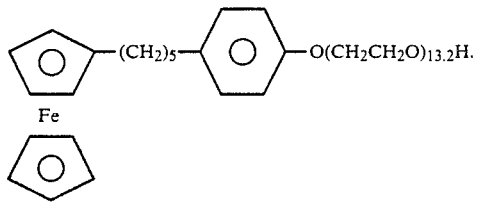

21. The ferrocene compound as claimed in claim 1, wherein the compound is of the formula

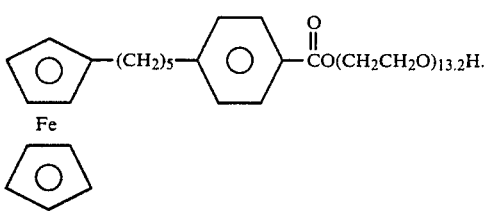

22. The ferrocene compound as claimed in claim 1, wherein the compound is of the formula

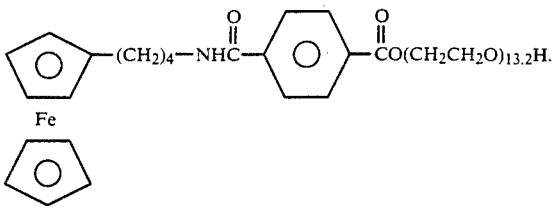

23. The ferrocene compound as claimed in claim 1, wherein the compound is a compound selected from the group consisting of

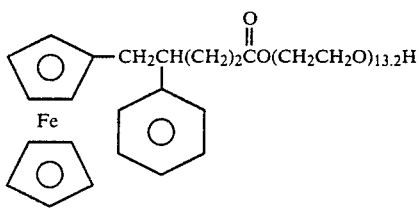

and

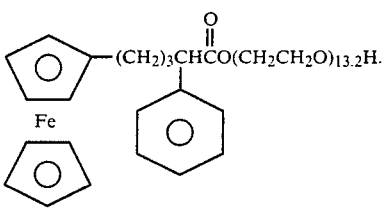

24. The ferrocene compound as claimed in claim 1, wherein the compound is a compound selected from the group consisting of

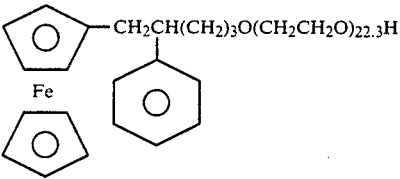

and

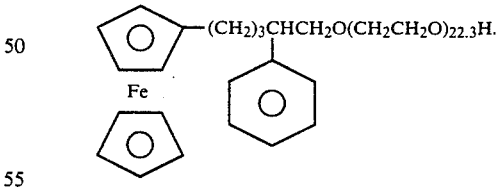

* * * * *